U S009239283B2

(12) United States Patent
Honda et al.

(10) Patent No.: US 9,239,283 B2
(45) Date of Patent: Jan. 19, 2016

(54) DEFECT INSPECTION METHOD AND DEVICE THEREFOR

(75) Inventors: Toshifumi Honda, Yokohama (JP); Yukihiro Shibata, Fujisawa (JP); Atsushi Taniguchi, Fujisawa (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 201 days.

(21) Appl. No.: 13/993,888

(22) PCT Filed: Nov. 8, 2011

(86) PCT No.: PCT/JP2011/075758
§ 371 (c)(1),
(2), (4) Date: Jul. 25, 2013

(87) PCT Pub. No.: WO2012/081338
PCT Pub. Date: Jun. 21, 2012

(65) Prior Publication Data
US 2013/0293879 A1      Nov. 7, 2013

(30) Foreign Application Priority Data
Dec. 13, 2010   (JP) .................................. 2010-276914

(51) Int. Cl.
*G01N 21/00* (2006.01)
*G01N 21/956* (2006.01)
*G01N 21/95* (2006.01)
*G01N 21/88* (2006.01)

(52) U.S. Cl.
CPC ............ *G01N 21/00* (2013.01); *G01N 21/8851* (2013.01); *G01N 21/9501* (2013.01); *G01N 21/956* (2013.01); *G01N 2021/8896* (2013.01)

(58) Field of Classification Search
CPC ............ G01N 21/8851; G01N 21/956; G01N 2201/0231
USPC ................ 356/237.1–237.6, 239.1, 240.1, 73
See application file for complete search history.

(56) References Cited

U.S. PATENT DOCUMENTS 5,463,459 A      10/1995   Morioka et al.
6,608,676 B1      8/2003   Zhao et al.
(Continued)

FOREIGN PATENT DOCUMENTS

JP      2000-105203      4/2000
JP      2001-512237      8/2001
(Continued)

OTHER PUBLICATIONS

JP Office Action for Japanese Application No. 2010-276914, issued on Mar. 4, 2014.
(Continued)

*Primary Examiner* — Gregory J Toatley
*Assistant Examiner* — Iyabo S Alli
(74) *Attorney, Agent, or Firm* — Baker Botts L.L.P.

(57) ABSTRACT

To process a signal from a plurality of detectors without being affected by a variation in the height of a substrate, and to detect more minute defects on the substrate, a defect inspection device is provided with a photoelectric converter having a plurality of rows of optical sensor arrays in each of first and second light-collecting/detecting unit and a processing unit for processing a detection signal from the first and the second light-collecting/detecting unit to determine the extent to which the positions of the focal points of the first and the second light-collecting/detecting unit are misaligned with respect to the surface of a test specimen, and processing the detection signal to correct a misalignment between the first and the second light-collecting/detecting unit, and the corrected detection signal outputted from the first and the second light-collecting/detecting unit are combined together to detect the defects on the test specimen.

15 Claims, 19 Drawing Sheets

(56) References Cited

U.S. PATENT DOCUMENTS

| | | |
|---|---|---|
| 7,916,288 B2 | 3/2011 | Nakao et al. |
| 2008/0218762 A1 | 9/2008 | Zhao et al. |
| 2009/0059216 A1* | 3/2009 | Shibata ................ G01N 21/956 356/237.4 |
| 2009/0195775 A1 | 8/2009 | Nakao et al. |
| 2011/0304848 A1 | 12/2011 | Tanaka et al. |
| 2012/0019816 A1 | 1/2012 | Shibata et al. |

FOREIGN PATENT DOCUMENTS

| | | |
|---|---|---|
| JP | 2005-221368 | 8/2005 |
| JP | 2006-010334 | 1/2006 |
| JP | 2006-515668 | 6/2006 |
| JP | 2009-010325 | 1/2009 |
| JP | 2009-156574 | 7/2009 |
| JP | 2009-180691 | 8/2009 |
| JP | 2010-190722 | 9/2010 |
| JP | 2010-256340 | 11/2010 |
| WO | WO 2004/031741 A2 | 4/2004 |

OTHER PUBLICATIONS

JPOA for JP Application No. 2010-276914, issued on Jun. 17, 2014.
KPOA for Korean Patent Application No. 10-2013-7015141, issued on Jun. 3, 2014.

* cited by examiner

DEFECT INSPECTION METHOD AND DEVICE THEREFOR

BACKGROUND

The present invention concerns a method of detecting a minute defect occurred on a test specimen and a device therefor, and more particularly relates to a defect inspection method suitable for detecting a minute defect occurred on a semiconductor wafer with a fine pattern formed on its surface and a device therefor.

A semiconductor wafer is made more and more multi-layered in structure as the shape of a pattern to be formed on the wafer is more and more refined with high-integration of a circuit, and the number of producing steps thereof is being steadily increased. In order to stably produce a highly reliable high-integrated circuit by surely forming the fine pattern on the wafer, it becomes important to confirm that the fine pattern is surely formed and a defect such as a foreign matter or the like does not occur by inspecting the wafer on which the pattern is formed.

As a means for inspecting the wafer with the pattern formed thereon, there exist, for example, a pattern inspection device of light-field-based optical system (a light-field pattern inspection device), a defect inspection device of dark-field-based optical system (a dark-field defect inspection device) and others.

Although the applications of the light-field pattern inspection device and the dark-field inspection device are different from each other in general, the dark-field defect inspection device has such a feature that throughput of inspection is higher than that of the light-field pattern inspection device.

In such a dark-field defect inspection device as mentioned above, how a more minute defect is to be detected at a higher speed without being affected by light scattered from the pattern formed on the wafer is one of problems.

As a means for solving this problem, in Japanese Patent Application Laid-Open No. 2000-105203 (Patent Document 1) and Japanese Patent Application Laid-Open No. 2001-512237 (Patent Document 2), there is a description that a wafer is obliquely irradiated with linear illumination light which is finely squeezed in one direction and light which has been scattered from a surface of the wafer with the linear illumination light is detected by a detection system above the wafer and detection systems disposed on its both sides while continuously moving the wafer in a direction orthogonal to a longitudinal direction of the illumination light, thereby detecting a defect on the wafer by using respective detection signals.

In addition, in Japanese Patent Application Laid-Open No. 2010-256340 (Patent Document 3), there is a description that a TDI (Time Delay Integration) sensor is used in a detection system and it is configured to asynchronously control a line rate of the TDI sensor and a stage scan speed to illuminate an object to be inspected with finely squeezed linear light so as to make only an arbitrary pixel line of the TDL sensor receive scattered light from the inspected object such that an aspect ratio of the size of a detection pixel can be controlled with a speed ratio of the line rate of the TDI sensor to the stage scan speed, thereby making inspection possible at a scan speed higher than the line rate of the TDI sensor.

Further, in Japanese Patent Application Laid-Open No. 2010-190722 (Patent Document 4), there is a description that a wafer is obliquely irradiated with linear illumination light which is finely squeezed in one direction, light which has been scattered upward from a surface of the wafer with the linear illumination light is collected while continuously moving the wafer in a direction orthogonal to a longitudinal direction of the linear illumination light and is branched in accordance with a state of polarization, light transmitted through a spatial filter is detected by filtering diffracted light and scattered light from a normal pattern by the arrayed spatial filter, thereby detecting a defect independently of polarization characteristics of scattered light from the defect.

SUMMARY

In order to efficiently detect the more minute defect and to classify the kind of the detected defect, a method of detecting it by separating a scattering orientation by utilizing scattering characteristics which are different depending on the kind of the defect can be conceived of. That is, by arranging detectors in a plurality of places and processing and combining together signals detected at the respective places, it becomes possible to actualize a signal that scattered light from a more minute defect which would be buried in noise in detection from one direction has been detected and it becomes possible to more finely classify the kind of the detected defect.

That the scattered light from the defect is detected by arranging the detectors in a plurality of directions as mentioned above is described in Patent Documents 1 and 2. In the configurations of the inspection devices described in FIG. 25 of Patent Document 1 and in FIG. 2 of Patent Document 2, the plurality of detectors are arranged obliquely relative to a normal direction of a substrate.

In the configurations described in Patent Documents 1 and 2, linear illumination light is irradiated to the substrate and scattered light from the substrate is detected while moving a stage with the substrate placed thereon in a direction perpendicular to a longitudinal direction of the linear illumination at a fixed speed. It is known that positional variations such as pitching (a vertical variation) and yoking (a lateral variation) occur on a table when the stage is moved at the fixed speed. Misalignment occurs in position on the substrate surface to be detected by the detectors arranged in different azimuth directions due to a variation in the height of the substrate caused by the pitching in these, and mutual positional misalignment occurs between signals that the same pattern formed on the substrate surface has been detected by the respective detectors. This becomes remarkable when detecting a more minute defect of about several tens nm or less.

However, in the inventions described in Patent Documents 1 and 2, nothing is considered with respect to positional misalignment of detection signals among the plurality of detectors which occurs with the variation in the height of the substrate.

In addition, in Patent Documents 3 and 4, that the defect on the substrate is detected by arranging the plurality of detectors in the different azimuth directions is not described.

An object of the present invention is to provide defect inspection method and device therefor making it possible to detect a more minute defect on a substrate by processing signals from a plurality of detectors which are arranged in plurality directions without being affected by the variation in the height of the substrate.

In order to solve the above-mentioned problem, in the present invention, in a defect inspection device including a stage unit which is movable at least in one direction with a test specimen placed thereon, a light irradiation unit which irradiates the test specimen placed on the stage unit with linearly shaped light from a direction inclined relative to a normal direction of a surface of the stage on which the test specimen is placed, a first light collecting/detecting unit which collects and detects light reflected/scattered in a first direction from the test specimen irradiated with the linearly shaped light by the light irradiation unit, a second light collecting/detecting unit which collects and detects light reflected/scattered in a second direction from the test specimen irradiated with the linearly shaped light by the light irradiation unit, a processing unit which processes a detection signal output from the first light collecting/detecting unit and a detection signal output from the second light collecting/detecting unit to detect a defect on the test specimen and a control unit for controlling the stage unit, the light irradiation unit, the first light collecting/detecting unit, the second light collecting/detecting unit and the processing unit, each of the first light collecting/detecting unit and the second light collecting/detecting unit has a photoelectric converter provided with a plurality of optical sensor arrays, the processing unit obtains misalignment of a focal position of the first light collecting/detecting unit relative to a surface of the test specimen by using detection signals from the plurality of optical sensor arrays of the first light collecting/detecting unit, obtains misalignment of a focal position of the second light collecting/detecting unit relative to the surface of the test specimen by using detection signals from the plurality of optical sensor arrays of the second light collecting/detecting unit, corrects the detection signal output from the first light collecting/detecting unit and the detection signal output from the second light collecting/detecting unit in accordance with the obtained misalignment of the focal position of the first light collecting/detecting unit and the obtained misalignment of the focal position of the second light collecting/detecting unit, combines together the detection signal output from the first light collecting/detecting unit and the detection signal output from the second light collecting/detecting unit which have been corrected to detect the defect on the test specimen.

In order to solve the above-mentioned problem, in the present invention, in a defect inspection device including a stage unit which is movable at least in one direction with a test specimen placed thereon, alight irradiation unit which irradiates the test specimen placed on the stage unit with linearly shaped light from a direction inclined relative to a normal direction of a surface of the stage on which the test specimen is placed, a first light collecting/detecting unit which collects and detects light reflected/scattered in a first direction from the test specimen irradiated with the linearly shaped light by the light irradiation unit, a second light collecting/detecting unit which collects and detects light reflected/scattered in a second direction from the test specimen irradiated with the linearly shaped light by the light irradiation unit, a processing unit which processes a detection signal output from the first light collecting/detecting unit and a detection signal output from the second light collecting/detecting unit to detect a defect on the test specimen and a control unit which controls the stage unit, the light irradiation unit, the first light collecting/detecting unit, the second light collecting/detecting unit and the processing unit, each of the first light collecting/detecting unit and the second light collecting/detecting unit has a photoelectric converter provided with a plurality of optical sensor arrays, the control unit controls the stage unit to continuously move the stage unit in the first direction and controls the photoelectric converter of the first light collecting/detecting unit and the photoelectric converter of the second light collecting/detecting unit to detect reflected and scattered light from the test specimen irradiated with the linearly shaped light by the light irradiation unit in synchronization with movement of the stage unit, and the control unit further controls the processing means to process detection signals output from the photoelectric converter of the first light collecting/detecting unit and the photoelectric converter of the second light collecting/detecting means at a timing different from the synchronization with movement of the stage unit and to combine together the detection signals which have been output from the photoelectric converter of the first light collecting/detecting unit and the photoelectric converter of the second light collecting/detecting unit and have been processed at the timing different from the synchronization, thereby detecting a defect like the test specimen.

Further, in order to solve the above-mentioned problem, in the present invention, a defect inspection method is configured by while moving a stage with a test specimen placed thereon in one direction, irradiating a surface of the test specimen with linearly shaped light which is long in a direction rectangular to the one direction that the stage moves from a direction inclined relative to a normal direction of the surface of the test specimen, collecting and detecting light reflected/scattered in a first direction from the surface of the test specimen irradiated with the linearly shaped light by a first light collecting/detecting unit provided with a plurality of optical sensor arrays, collecting and detecting light reflected/scattered in a second direction from the surface of the test specimen irradiated with the linearly shaped light by a second light collecting/detecting unit provided with a plurality of optical sensor arrays, obtaining misalignment of a focal position of the first light collecting/detecting unit relative to the surface of the test specimen by using detection signals from the plurality of optical sensor arrays and output from the first light collecting/detecting unit and obtaining misalignment of a focal position of the second light collecting/detecting unit relative to the surface of the test specimen by using detection signals from the plurality of optical sensor arrays and output from the second light collecting/detecting unit, correcting the detection signal output from the first light collecting/detecting unit and the detection signal output from the second light collecting/detecting unit in accordance with the misalignment of the focal position of the first light collecting/detecting unit and the misalignment of the focal position of the second light collecting/detecting unit which have been so obtained, and combining together the detection signal output from the first light collecting/detecting unit and the detection signal output from the second light collecting/detecting unit which have been so corrected to detect a defect on the test specimen.

Still further, in order to solve the above-mentioned problem, in the present invention, a defect inspection method is configured by while moving a stage with a test specimen placed thereon in one direction, irradiating a surface of the test specimen with linearly shaped light which is long in a direction rectangular to the one direction that the stage moves from a direction inclined relative to a normal direction of the surface of the test specimen, collecting and detecting light reflected/scattered in a first direction from the surface of the test specimen irradiated with the linearly shaped light by a first light collecting/detecting unit having a plurality of optical sensor arrays in synchronization with movement of the stage in the one direction, collecting and detecting light reflected/scattered in a second direction from the surface of the test specimen irradiated with the linearly shaped light by a second light collecting/detecting unit having a plurality of optical sensor arrays in synchronization with movement of the stage in the one direction and processing detection signals output from a photoelectric converter of the first light collecting/detecting unit and a photoelectric converter of the second light collecting/detecting unit at a timing different from the synchronization with the movement of the stage and combining together the detection signals output from the photoelectric converter of the first light collecting/detecting unit and the photoelectric converter of the second light collecting/detecting unit which have been processed at the timing different from the synchronization to detect a defect on the test specimen.

According to the present invention, it becomes possible to process the detection signals of the plurality of detectors by combining them together without being affected by the variation in the height direction of the substrate under inspection and therefore it becomes possible to detect more minute defect.

DESCRIPTION OF THE PREFERRED EMBODIMENTS

In the following, embodiments of the present invention will be described using the drawings.

Embodiment 1

A first embodiment of the present invention will be described using FIGS. 1 to 22.

Figure 1:
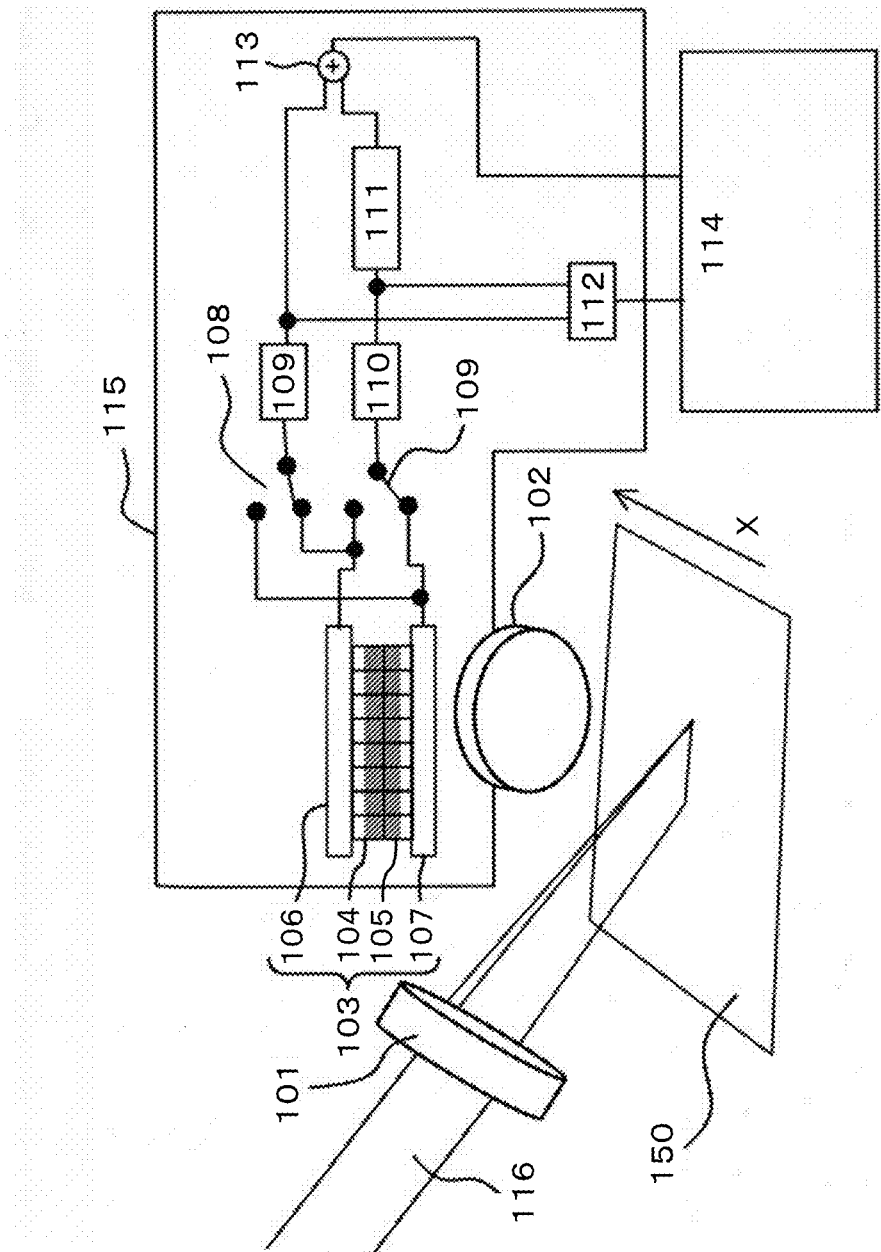
FIG. 1 is a block diagram explaining the principle of an embodiment 1 of the present invention.

FIG. 1 is a diagram explaining the principle of the present embodiment. In the present embodiment, illumination light 116 is squeezed in one direction by a lens unit 101 so as to be shaped into light which is parallel in a direction perpendicular to it and is obliquely irradiated to a surface of a test specimen 150 with a fine pattern formed. In inspection, the test specimen 150 is moved by a later described stage means at a fixed speed in an arrow direction.

102 is a detection optical system which collects light reflected/scattered in a direction of the detection optical system 102 in reflected/scattered light from the test specimen 150 irradiated with the linearly shaped illumination light 116 and forms an image of a linearly irradiated region of the test specimen 150 on detection element arrays 104, 105 of a detector 115.

In the detector 115, there are a two-stage sensor (two-dimensional CCD or Dual Line Sensor) 103 having the detection element arrays 104, 105 and respectively providing read out registers 106 and 107 for reading out signals for them, switches 108 and 109 for switching outputs from the read out registers 106 and 107 of the two-stage sensor in accordance with a moving direction of the test specimen 150, A/D conversion units 109 and 110 for converting analog signals simultaneously output from the read out registers 106 and 107 into digital signals, an FIFO (First In First Out) memory 111 for temporarily storing the digital signal output from the A/D converter 110 and outputting it in timing with the digital signal output from the A/D converter 109, and an adder 113 for adding together and outputting an output signal from the FIFO memory 111 and the output signal from the A/D converter 109, 112 is a height misalignment information calculation unit for obtaining information on height misalignment of the test specimen 150 by using the output signal from the A/D converter 109 and the output signal from the A/D converter 110. 114 is an image processing unit for receiving an output signal from the detector 115 to detect a defect on the test specimen 150.

Figure 2:
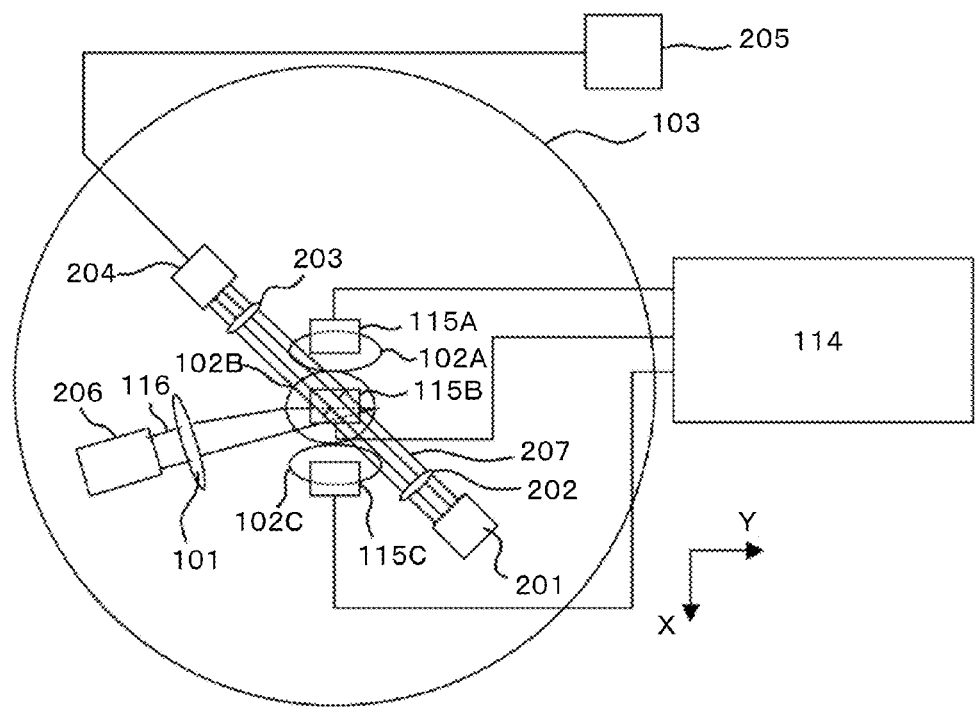
FIG. 2 is a plan view showing a schematic configuration of an optical system of the embodiment 1 of the present invention.

FIG. 2 is a plan view showing a configuration of an optical system of a defect inspection device according to the present embodiment. In the optical system of the defect inspection device according to the present invention, a light source 206 and the lens unit 101 for linearly shaping the illumination light 116 emitted from the light source 206 into a beam are provided on the side of an illumination optical system. The light source 206 emits ultraviolet laser such as UV light, DUV light or the like. On the other hand, the detection optical system 102 is configured by being provided with a first oblique detection optical system 102A and a first detector 115A, an upward detection optical system 102B and an upward detector 115B, and a second oblique detection optical system 102C and a second detector 115C. Output signals from the first detector 115A, the upward detector 115B and the second detector 115C are input into the image processing unit 114 and are processed.

In addition, the defect inspection device according to the present embodiment is provided with a height detection unit for detecting the height of the surface of the test specimen 150. The height detection unit is configured by a light source unit 201 for emitting a plurality of linear light patterns 207, a light collecting lens 202 for collecting and radiating the linear light patterns 207 emitted from the light source unit 201 to the surface of the test specimen 150 from a direction inclined relative to a normal direction of the test specimen 150, a light collecting lens 203 for collecting reflected light (regularly reflected light) from the test specimen 150 irradiated with the plurality of linear light patterns 207 and a photo-detector 204 for detecting the reflected light so collected, and a height detection unit 205 for receiving and processing a signal that the reflected light from the test specimen 150 has been detected by the photo-detector 150 to extract height information of the test specimen 150.

Figure 3A:
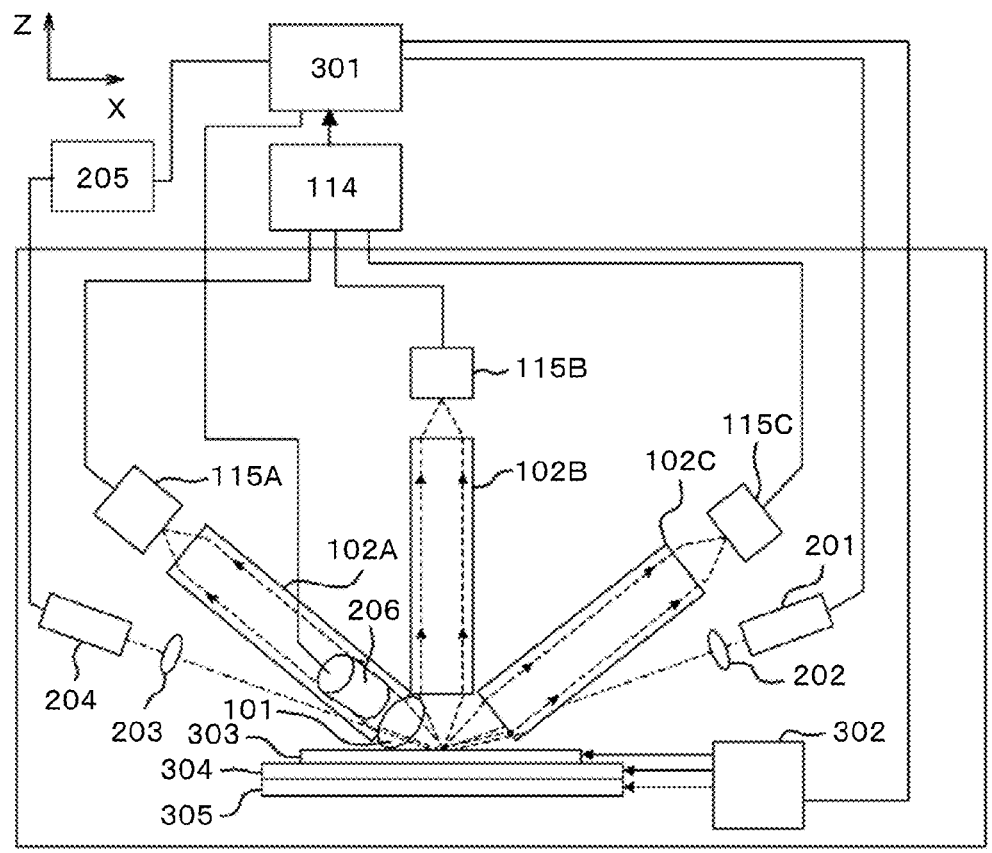
FIG. 3A is a front view showing the schematic configuration of the optical system of the embodiment 1 of the present invention.

FIG. 3A is a front view showing a configuration of an inspection optical system 100 of the defect inspection device according to the present embodiment. 303 is a Z-stage which is movable in a height direction, 304 is an X-stage which is movable in an X direction, 305 is a Y-stage which is movable in a Y direction perpendicular to a paper surface, and movements thereof are respectively controlled by a stage control means 302. The test specimen 150 is placed on the Z-stage 303. In the configuration shown in FIG. 3, each of the first oblique detection optical system 102A, the upward detection optical system 102B and the second oblique optical system 102C is provided with an objective lens 1021, a spatial filter 1022, a focusing lens 1023, a polarizing filter 1024, and an imaging lens 1025, and shields a diffracted light pattern by diffracted light which is generated by radiating light to a fine repeated pattern on the test specimen 105 by the spatial filter 1022 and images reflected/scattered light transmitted through the spatial filter 1022 by the imaging lens 1025 on a detection surface of the detector 115 as shown in FIG. 3C. Since the configuration shown in FIG. 3C is common to the first oblique detection optical system 102A, the upward detection optical system 102B and the second oblique detection optical system 102C, notation of the last A, B, C of the respective constitutional components are omitted.

Figure 3B:
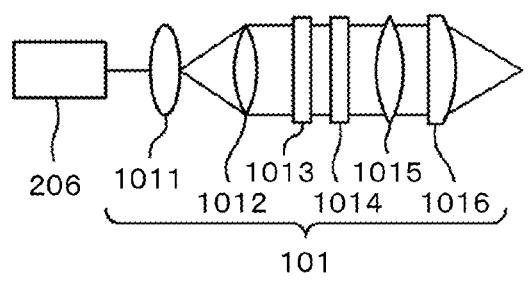
FIG. 3B is a front view showing a schematic configuration of an illumination optical system of the embodiment 1 of the present invention.
Figure 3C:
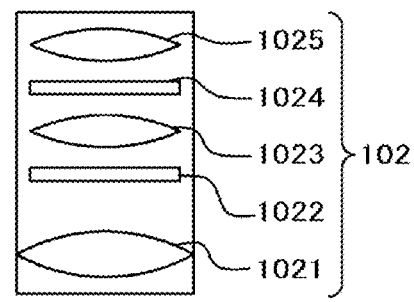
FIG. 3C is a front view showing a schematic configuration of a detection optical system of the embodiment 1 of the present invention.

In addition, a configuration of the illumination optical system side is shown in FIG. 3B. The illumination optical system is provided with the light source 206 for emitting a laser beam and the lens unit 101. The lens unit 101 is provided with a beam expander 1011 for expanding a diameter of the laser beam emitted from the light source 206, a collimator lens 1012 for collimating the diameter-expanded laser, a polarizing plate 1013 for adjusting a polarized state of the laser, a light amount adjusting unit 1014 for adjusting a light amount, a condenser lens 1015, and a cylindrical lens 1016 for condensing the diameter-expanded laser beam in one direction and shaping it into linear light which is maintained in a parallel state in a direction perpendicular to it.

301 is a general control unit for controlling the light source 206 on the illumination side, the light source unit 201 of the height detection unit, and the stage control means 302 and receives outputs from the image processing unit 114 and the height detection unit 205 to output a result of inspection of the test specimen 150.

In the configurations shown in FIG. 2 and FIG. 3, in inspection, the x-stage 304 is controlled by the stage control means 302 to move it in one direction at a constant speed, and detection signals are output from the first detector 115A, the upward detector 115B and the second detector 115C in synchronization with movement of the X-stage 304. When inspection up to an end on the test specimen 150 is completed by moving the X-stage 304, the Y-stage 305 is controlled by the stage control means 302 to shift the inspection region of the test specimen 150 to the next inspection region. Next, the X-stage 304 is controlled by the stage control means 302 to move it at a constant speed in a reverse direction (a −x direction) to the one direction. The entire surface of the test specimen 150 can be inspected by repeating the above moving.

Figure 4:
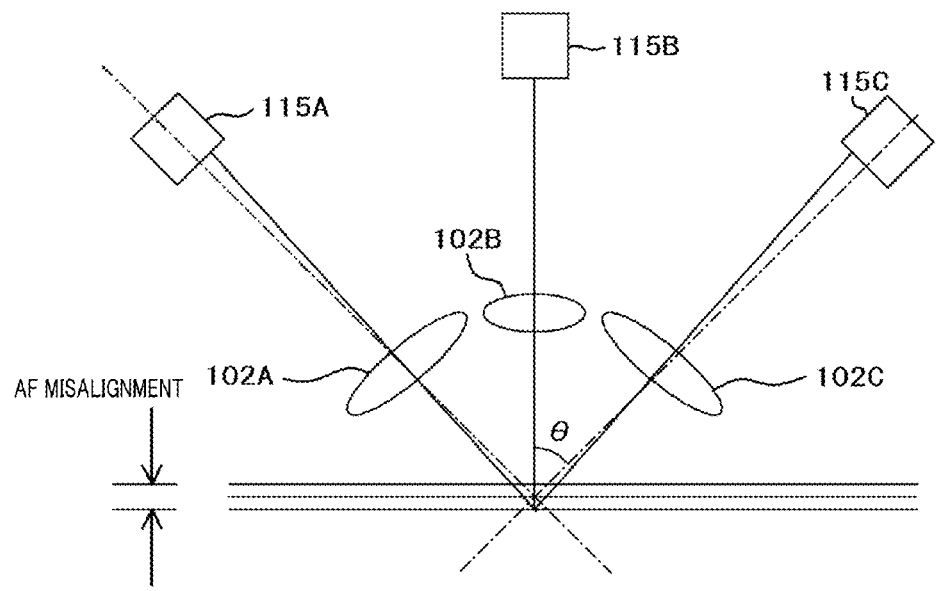
FIG. 4 is a block diagram of the detection optical system, explaining misalignment in detection position on a sensor caused by AF misalignment.

When driving the X-stage 304 to move the test specimen 150 in the X direction or the X direction at the constant speed as mentioned above, a variation in the height in the vertical direction which is called pitching occurs on the X-stage 304. In addition, the variation in the height in the vertical direction also occurs by two-dimensional deflection of the test specimen. When such a variation in the height occurs on the X-stage 304 during inspection, incident angles of the light reflected/scattered from the surface of the test specimen 150 and incident upon the first oblique detection optical system 102A and the second oblique detection optical system 102C are changed as shown in FIG. 4 and misalignment in the position for receiving the reflected/scattered light from the surface of the test specimen 150 occurs on respective light receiving surfaces of the first detector 115A and the second detector 115C. On the other hand, no misalignment occurs on a light receiving position for light reflected/scattered from the test specimen 105 and incident upon the upward detector 115B.

In practice, the stage control means 302 is controlled by the general control unit 301 on the basis of height information of the surface of the test specimen 150 detected by the height detection unit configured by the light source unit 201 to the height detection unit 205 shown in FIG. 2 or 3, and thereby the position (the height) is adjusted in the Z-axis direction of the Z-stage 303. However, misalignment (AF (Auto Focus) misalignment) in a height direction occurs due to offset of adjustment, a time-lag and the like. If signals from the respective detectors are combined together and processed in a state the AF misalignment occurring, an image will become blurred by the amount of the AF misalignment and as a result accuracy in defect detection will be degraded.

As a method of reducing the AF misalignment, there exists a method of narrowing the line width of the linear illumination light to illuminate the test specimen 150. However, as described later, the influence of the AF misalignment cannot be sufficiently reduced simply by narrowing the line width of the illumination light and the influence of the AF misalignment on the accuracy in detection cannot be sufficiently eliminated and will be left behind.

Figure 5:
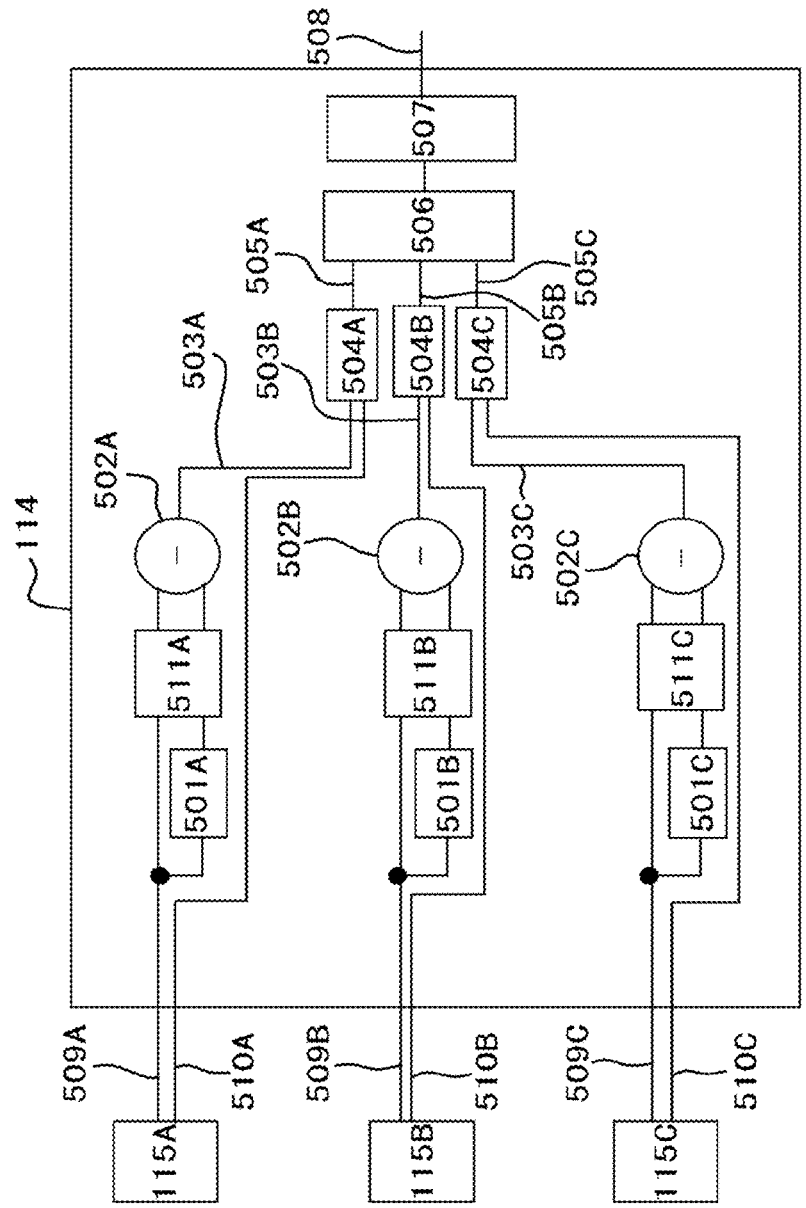
FIG. 5 is a block diagram showing a configuration of an image processing means concerning the embodiment 1 of the present invention.

FIG. 5 is a block diagram showing a configuration of the image processing means 114.

From the signal output from the first detector 115A in synchronization with movement of the X-stage 304 in the X direction, a signal 509A which is output from the adder 113 and is addition of outputs from the two detection element arrays 104 and 105 is branched into two and one of them is input into a buffer memory designated by 501A. 501A is the FIFO type buffer memory which outputs an image which delays integral multiples of a die. Incidentally, among them, noise reduction can be promoted by superposing images which are away from each other by a plurality of dies. 511A is a first position alignment processing unit which detects positional misalignment between images which are away from each other by integral multiples of the die and outputs the branched two images such that positional misalignment does not occur and inputs them into a differentiator 502A. A signal that patterns of the same shape on the test specimen 150 have been detected or a signal that patterns in the same regions of adjacent dies on the test specimen 150 have been detected and which has been input into the buffer memory 501A in advance is used as a reference signal, a difference with the reference signal is calculated (cell comparison or die comparison), and a calculated differential image signal 503A is input into a second position alignment circuit unit 504A. In addition, in outputs from the first detector 115A, an output signal 510A from the height misalignment information calculation unit 112 is also input into the position alignment circuit unit 504A, correction of the amount of height misalignment is performed on the separately input differential image signal 503A, and an image of the defect candidate is output.

Similarly, respective signals which have been output from the upward detector 115B and the second detector 115C in synchronization with movement of the X-stage 304 in the x direction are processed, difference images 505B, 505C (images of the defect candidates) which have been corrected by the amount of height misalignment by position alignment circuit units 504B and 504C are extracted and are input into an integration determining unit 506. In the integration determining unit 506, the difference images 505A to 505C (the images of the defect candidates) which have been corrected by the amount of the height misalignment are integrated to generate one image. The image generated by the integration determining unit 506 is compared with a threshold value by a threshold value determination unit 507, and a defect signal 508 which has been extracted as a result of comparison is output to the general control unit 301.

Figure 6:
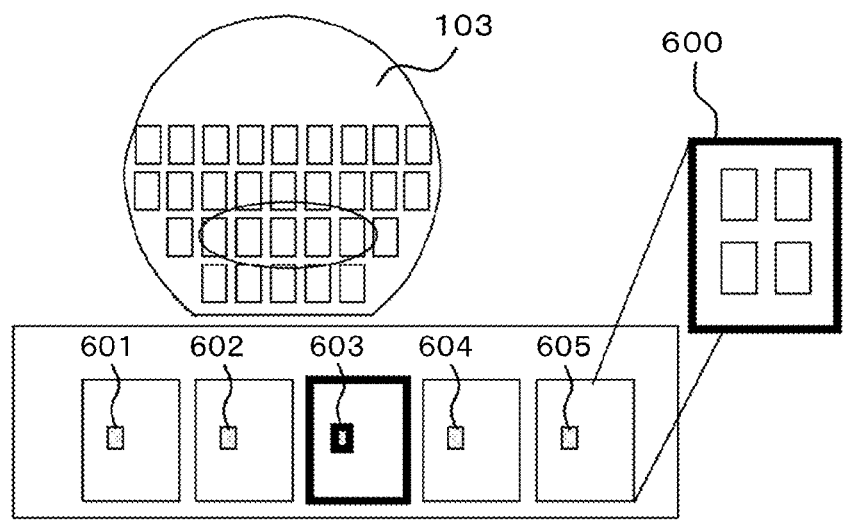
FIG. 6 is a plan view of a wafer and an enlarged diagram of a chip formed on the wafer.

FIG. 6 visibly shows die comparison to be executed by the differentiators 502A to 502C. A plurality of dies (chips) 600 are formed on a semiconductor wafer which is the test specimen 150 and patterns 601 to 605 of the same shape are formed on corresponding places on the respective dies. In the differentiators 502A to 502C, for example, an image of a die pattern 603 is compared with an image of a die pattern 604 formed on the chip adjacent to the chip on which the die pattern 603 is formed and is used as reference image to calculate a difference image between the both images is calculated.

Figure 7:
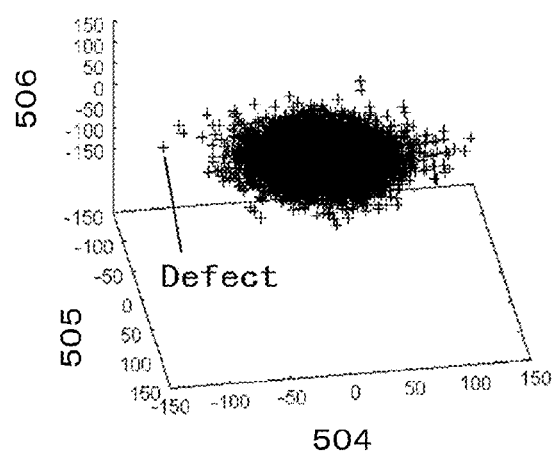
FIG. 7 is a graph showing an example that signal feature amounts of defect candidates detected by three detection optical systems of the embodiment 1 of the present invention are plotted in a three-dimensional space.

FIG. 7 shows an example that image characteristic amounts extracted from the respective defect candidate images which have been output from the respective position alignment circuit units 504A to 504C, to which the respective difference images are input from the respective position alignment circuit units 504A to 505C, to be executed by the combination determination unit 506 are plotted in a three-dimensional space. When the image characteristic amounts of the defect candidates are plotted in the three-dimensional space as mentioned above, although the characteristic amounts of images of parts which are not true candidates are distributed densely on the center, the characteristic amount of an image including a defect is present at a part separated from the distribution of the difference images calculated from an image of a normal part. Therefore, the true defect can be detected by integrating the images of the defect candidates obtained from the respective detectors, plotting them in the three-dimensional space as shown in FIG. 7 and extracting outliers.

However, in order to accurately detect the defect by integrating the images of the defect candidates obtained from the respective detectors and plotting features extracted from the integrated images in a multi-dimensional space as shown in FIG. 7, it is essential that positional misalignment of the defect candidate obtained from each detector be corrected, that is, the alignments of the defect candidates obtained from the respective detectors match one another. However, it is extremely difficult to align the images of, for example, 115A to 115C with one another by using a generally performed image matching technique. Because detection conditions of the respective images are different from one another and therefore patterns appeared on the respective images are different from one another.

Figure 8:
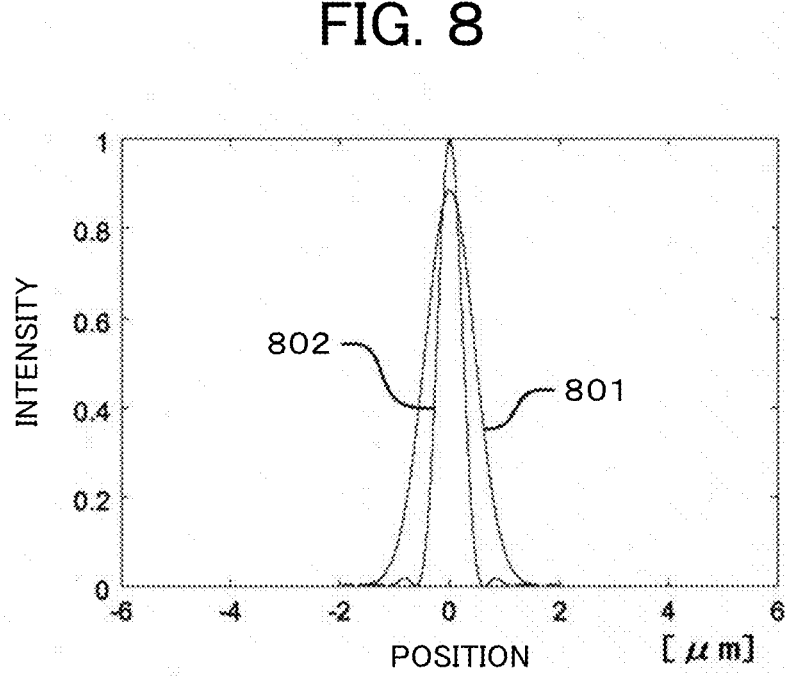
FIG. 8 is a graph showing a profile of illumination and a PSF (Point Spread Factor) of the detection system when assuming that a pixel size is infinitesimal.

FIG. 8 is a graph that a profile 801 of illumination and a profile 802 of the detection system relative to a stage scanning direction are plotted. Here, in calculation of the profile 801 of the illumination, it is assumed that a beam width is 1.8 µm, the illumination is oblique illumination and the intensity of the illumination exhibits the Gaussian distribution. In addition, in calculation of the profile 802 of the detection system, assuming that scattered light by the Fraunhofer diffraction is generated from the pattern on the test specimen 150 by taking a case where detection is performed through an optical system which is arranged in a direction inclined by 45 degrees relative to the normal direction of the test specimen and is 0.5 in NA (Numerical Aperture) with the pixel size of the detector made infinitesimal as an example, a Point Spread Function (PSF) d(x) of the optical system is obtained by (Numerical Formula 1).

$$y(x) = \frac{2\pi N A x \sin\theta}{\lambda}$$ (Numerical Formula 1)

$$d(x) = d_0(J1(y(x))/y(x))^2$$

where
λ: wavelength
χ: distance from center
θ: detection system angle from test specimen normal direction From the graph in FIG. 8, it is shown that the illumination of the oblique illumination system relatively spreads out when compared with the PSF of the detection system and a sufficient resolution of the image cannot be obtained simply by the illumination system relative to the stage scanning direction. In order to promote improvement of resolution of the device, it is effective to improve the resolution of the detection system.

Although a case where calculation is performed by making the pixel size of the detector infinitesimal is shown on the graph in FIG. 8, in actual, the pixel of the detector has a finite size. Therefore, in a case where calculation is performed by setting the pixel size of the detector 115C to 2.5 μm for later described reasons and other conditions are set as in the case in FIG. 8 as shown in FIG. 9A, the result is as shown by a graph in FIG. 9B.

Figure 9A:
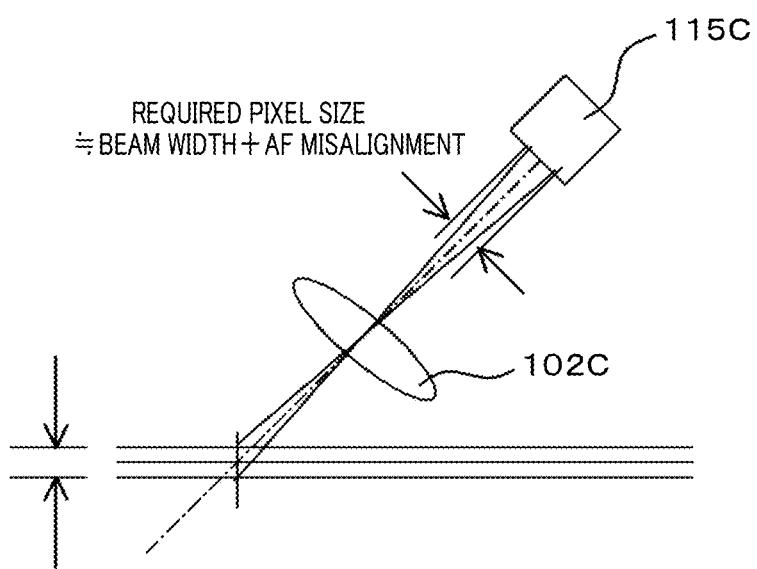
FIG. 9A is a block diagram of the detection optical system, explaining misalignment in detection position occurring by AF misalignment on an obliquely arranged sensor.

Here, assuming that misalignment of ±0.5 μm has occurred with the AF misalignment as shown in FIG. 9A because the test specimen 150 is continuously moved in the X direction and the height of the surface of the test specimen 150 is varied, the pixel size of the detector 115C which is required to allow the AF misalignment of ±0.5 μm when light of 1.8 μm in beam width has been irradiated should be 1.8+1.0/sqrt(2) =2.5 μm on the wafer.

Figure 9B:
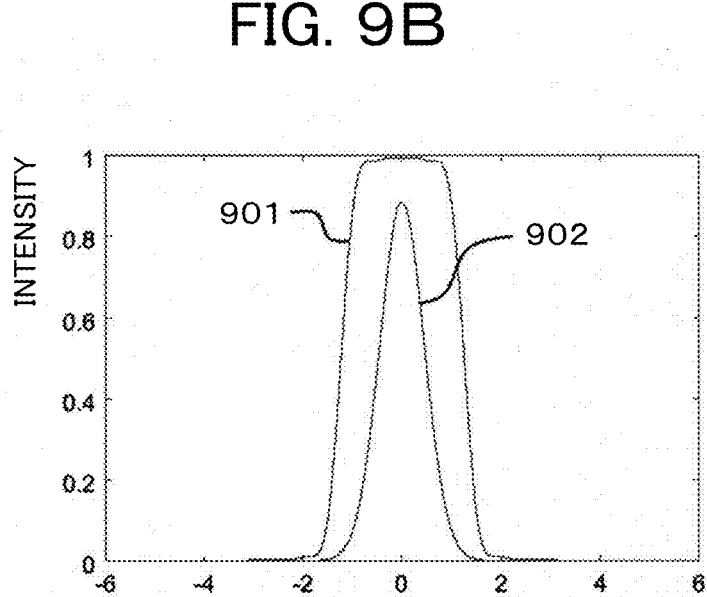
FIG. 9B is a graph showing the PSF of the detection system when taking a beam profile of linear illumination light and the pixel size into account.

The PSF of the detection system at that time is obtained by convolution of the PSF of the detection system as expressed by the (Numerical Formula 1) and pixel size as expressed by (Numerical Formula 2), and exhibits characteristics as shown in FIG. 9B.

$$rect(x) = \begin{cases} 1, & \text{if } |x| < 1/2 \\ 0 & \text{otherwise} \end{cases}$$ (Numerical Formula 2)

$$PSF(x) = rect(x/p) \otimes d(x)$$

where
P is the pixel size

In the graph shown in FIG. 9B, the resolution of the detection system is worsened in comparison with that of the illumination system shown in FIG. 8. That is, it is found from the graph in FIG. 9B that in a case where the detector having the finite pixel size is used in such a simple configuration as shown in FIG. 9A, the resolution of the illumination light in the beam line width direction (the stage moving direction) is determined by the resolution of the illumination system.

Figure 10:
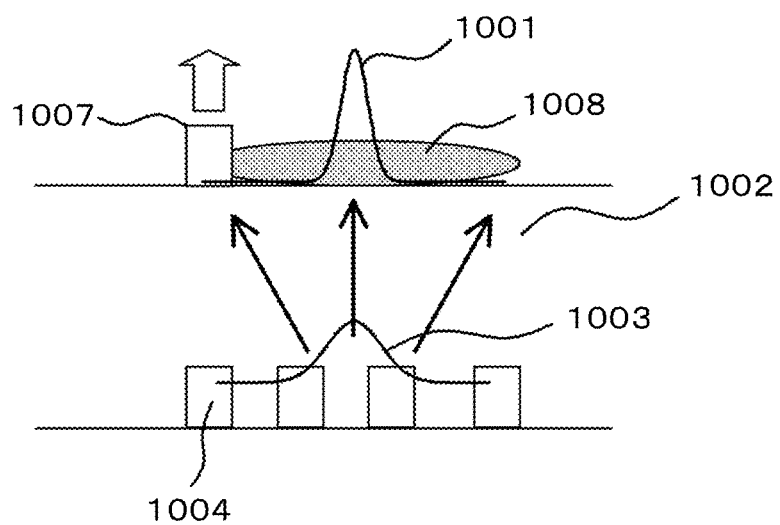
FIG. 10 is a sectional diagram of a semiconductor wafer with a pattern formed thereon.

FIG. 10 shows an example that a fine pattern 1004 is formed on a lower layer, an optically transparent thin film 1002 such as a silicon dioxide (SiO2) film or a silicon nitride (SiN) film is formed thereon, and a pattern 1007 is formed on a surface as the test specimen 150. In a case where illumination light having such a beam profile as denoted by 1001 has been irradiated to the test specimen 150 having such a sectional structure, the illumination light is transmitted through the optically transparent film 1002, is reflected/scattered by the lower-layer fine pattern 1004 and is transmitted through the optically transparent film 1002 turning to light having such a beam profile as denoted by 1003, and it interferes with incident light, resulting in such a distribution characteristic as denoted by 1008.

In a case where the test specimen 150 has such a structure that the influence of the reflected light from the base pattern is no negligible, it occurs that the resolution of the illumination system is lowered in appearance.

In order to avoid occurrence of such a phenomenon as mentioned above, it is necessary to improve the resolution of the detection system. In order to improve the resolution of the detection system, it is found that it is effective to reduce the pixel size of the detection system as apparent from comparison between FIG. 8 and FIG. 9B.

Figure 11A:
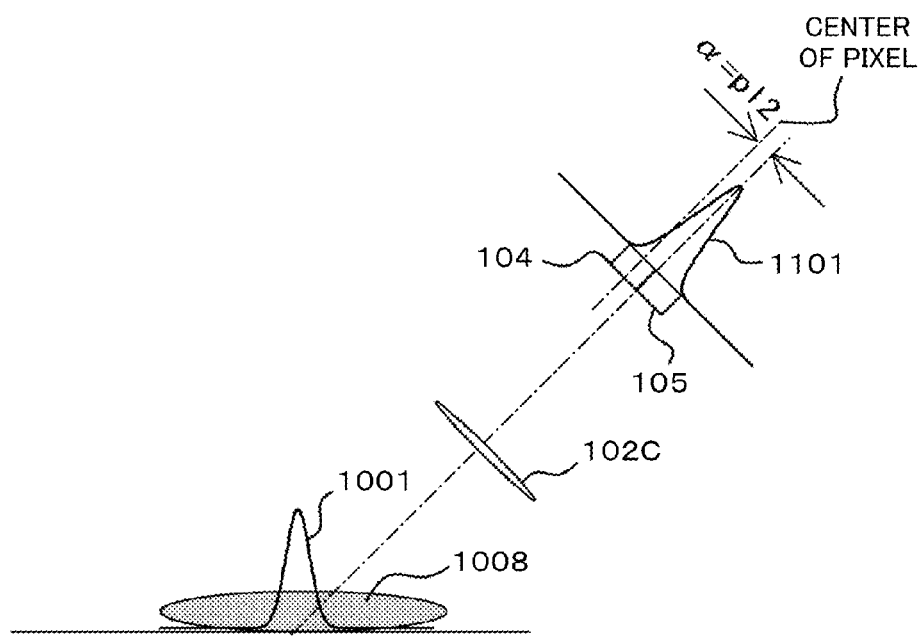
FIG. 11A is a block diagram of the detection optical system showing a relationship between the obliquely arranged sensor and reflected/scattered light from a test specimen in the embodiment 1 of the present invention.

FIG. 11A shows a state that similarly to the configuration shown in FIG. 9A, two pixels 104 and 105 are arranged and the size thereof is set to 1.25 μm which is one half of that in the case in FIG. 9A. It shows a state that the positions of a region to be irradiated with illumination light on the test specimen 150 and the pixels of the detection system are adjusted such that the center of the beam irradiated to the test specimen 150 is projected onto the middle between the two pixels 104 and 105.

Figure 11B:
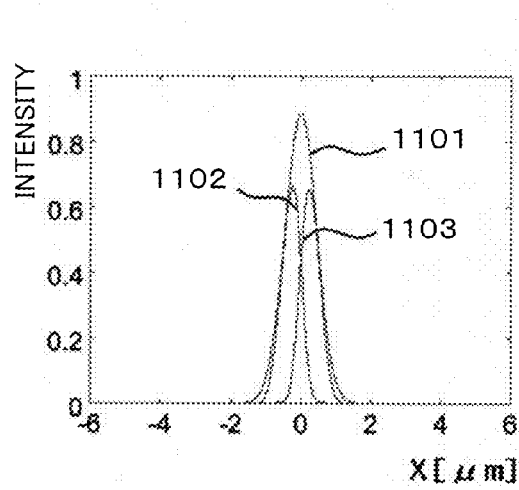
FIG. 11B is a graph showing a relationship between the beam profile of the linear illumination light and the PSF of the illumination system in the embodiment 1 of the present invention.

A beam profile of the illumination light and distributions of reflected/scattered light detected by the respective pixels 104 and 105 in the configuration shown in FIG. 11A are shown in FIG. 11B.

At that time, a profile 1101 of the illumination is expressed by (Numerical Formula 3)

$$i(x) = i_0 \exp\frac{x^2}{2(w/4)}$$ (Numerical Formula 3)

where
w: line width of illumination

On the other hand, the PSF when the pixel size of the detection system is made infinitesimal is expressed by (Numerical Formula 4).

$$I(x) = I_0 \frac{J_1(2\pi N A x \sin\theta/\lambda)^2}{\pi N A x \sin\theta/\lambda}$$ (Numerical Formula 4)

However, in actual, the pixel of the detection system has a finite size and when taking this into account, the PSF of the detection system is expressed by ((Numerical Formula 5).

$$PSF(x) = 1(x)(rect((x\pm\alpha)/p)1(x))$$ (Numerical Formula 5)

p: pixel size in the stage moving direction
α:p/2

Here, assuming that 2S is a moving amount of the stage synchronizing with acquisition of images of one line of the detection system having a multi-stage line sensor, in a case where i(x) obtained by the numerical formula 3 is almost constant, a shift amount can be set to ½ of the pixel size as in the case where it is detected by a general multi-stage line sensor (for example, a TDI sensor (Time Delay Integration sensor)). However, when the beam profile 1101 is made steeper by more finely squeezing the width of the illumination light, the shift amount is not determined by the pixel size, but it is determined by the beam profile of the illumination light and the resolution of the detection system to be expressed as shown by (Numerical Formula 6).

$$s = \frac{\int_{-\infty}^{\infty} xPSF(x)dx}{\int_{-\infty}^{\infty} PSF(x)dx}$$ (Numerical Formula 6)

While in a generally used TDI sensor, the shift amount which is denoted by s is ½ of the pixel size, when the configuration of the present invention is adopted, s becomes smaller than ½ of the pixel size. This is almost equivalent to that the pixel size as the system is reduced and even in a case where a large pixel size is used, a high resolution can be obtained. In this situation, in a case where the moving amount is moved by the amount equal to the pixel size on the test specimen as in the case where the general TDI sensor is utilized, the resolution of the pixel is degraded.

Figure 11C:
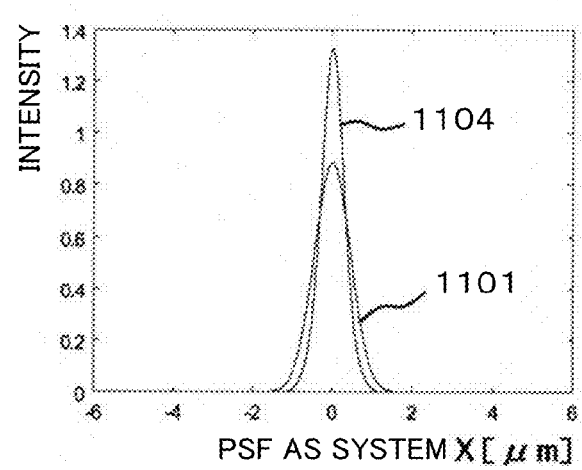
FIG. 11C is a graph showing a relationship between the beam profile of the linear illumination light and the PSF as a system that an amount of misalignment from the center of the illumination system is corrected in the embodiment 1 of the present invention.

FIG. 11C shows a graph that the PSF as the system is plotted by superposing with the beam profile of the illumination light. In this case, the FSF as the system is obtained by adding the distributions of the reflected/scattered light detected by the respective pixels 104 and 105 by shifting them by the shift amount from the center obtained on the basis of (Numerical Formula 6) (the above shifting means controlling by the general control unit 301 to make it synchronize with movement of the X-stage 304 in the X-direction so as to let the multistage line sensor 103 have a time delay relative to a synchronous signal for detecting the reflected/scattered from the test specimen 150). It is seen from this result that the resolution of the detection system is greatly improved comparing to the case shown in FIG. 9B.

Figure 12:
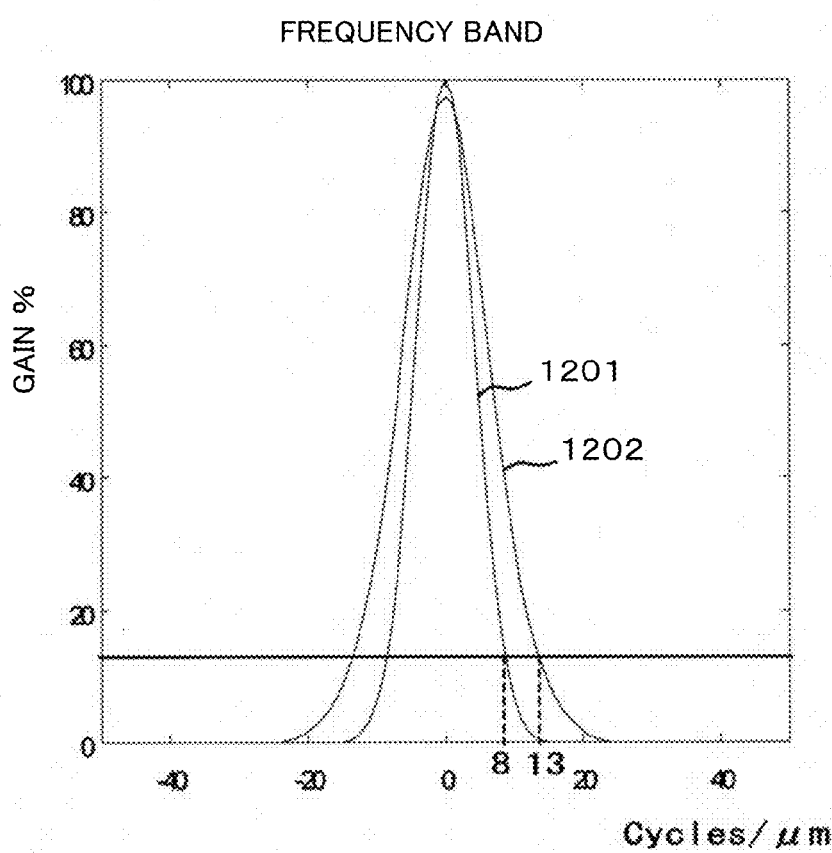
FIG. 12 is a graph showing a relationship between the resolution of a linear illumination system alone and the resolution of the illumination system in the embodiment 1 of the present invention.

FIG. 12 shows a graph that superposes the characteristics of the resolution attained by thinning the illumination light and the characteristics of the resolution of the present embodiment in which the resolution of the detection system has been improved by using the two-stage line sensor for the thinned illumination light.

It can be seen that the resolution is improved by adopting the detection system using the two-stage line sensor according to the present embodiment.

Figure 13A:
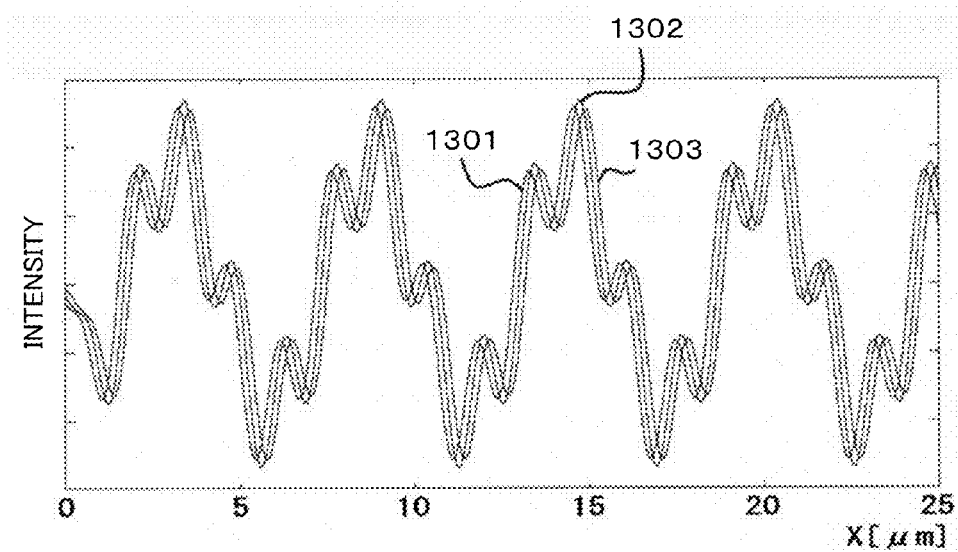
FIG. 13A is a graph showing sensor outputs when reflected/scattered light from a repeated pattern on a test specimen has been detected in the presence of AF misalignment in the embodiment 1 of the present invention.

FIG. 13A shows a result of the simulation of sensor outputs in a case where the AF misalignment is occurring and in a case where the AF misalignment is not occurring when test patterns are illuminated with thinned light by the optical system as shown in FIG. 11A using the two-stage line sensor. Results of the simulation of a sensor output 1302 free from the AF misalignment, a sensor output 1301 when the AF misalignment of −0.5 µm is occurring, and a sensor output when the AF misalignment of +0.5 µm is occurring are shown. It can be seen that the detection signal greatly varies by the AF misalignment. While this variation range 6 of the signal is ±0.5/sqrt(2)=±0.35 (µm) when adding them by reducing the shift amount of the image to one half of the pixel size by the conventional manner using the two-stage sensor as shown in FIG. 11A, the variation range δ can be reduced down to 0.18 µm when setting the shift amount of the image of the two-stage sensor to the value calculated by using (Numerical Formula 5) (the line width of illumination: 1.5 µm, the pixel size: 1.25 µm) as in the present embodiment.

Figure 13B:
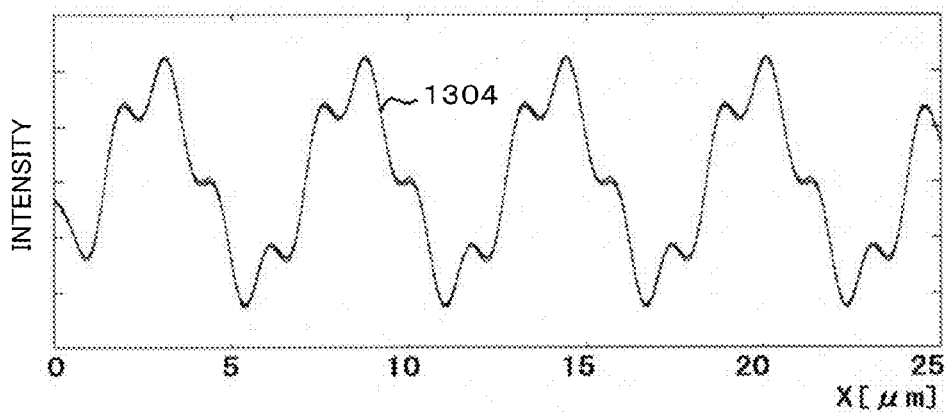
FIG. 13B is a graph showing a sensor output when reflected/scattered light from a repeated pattern on a test specimen has been detected in the presence of AF misalignment in detection by a conventional TDI sensor.

On the other hand, FIG. 13B shows a result of the simulation of a sensor output in a case where the AF misalignment which is the same as that in the case shown in FIG. 13A has occurred when using the conventional detection system that the pixel size is 2.5 µm as shown in FIG. 9A. In this case, since the pixel size is large enough to cover the variation amount of beam position caused by the AF misalignment, no change occurs in the position of the pattern to be detected regardless of occurrence of the AF misalignment. However, since the pixel size is large in the case in FIG. 13B, the sensitivity of defect detection is reduced in comparison with the case in FIG. 13A.

Figure 14A:
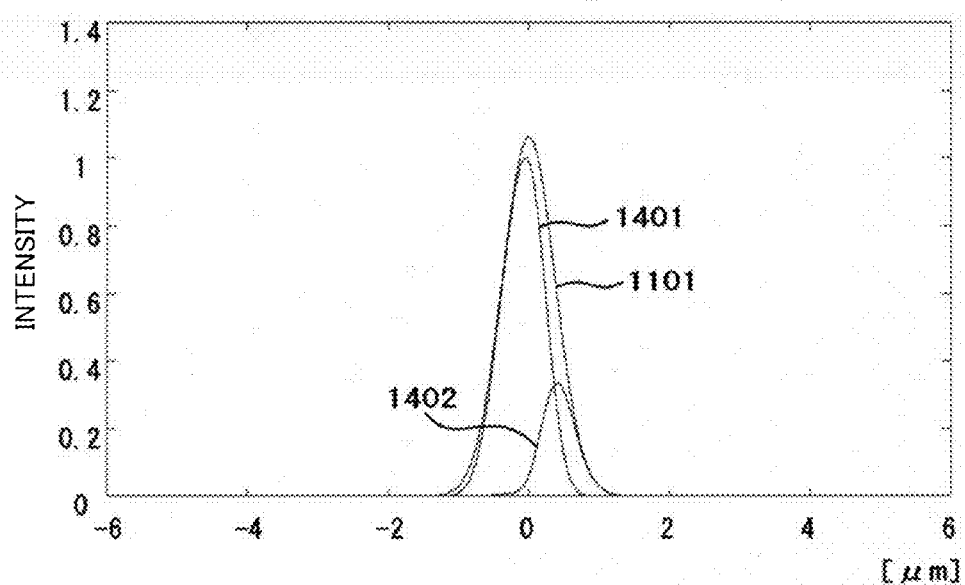
FIG. 14A is a graph showing output waveforms of each sensors in a case where the AF misalignment has occurred when using a two-stage sensor in the embodiment 1 of the present invention.

FIG. 14A shows output waveforms from the pixel arrays 104 and 105 of the two-stage sensor 103 in occurrence of the AF misalignment. As described in FIG. 11A, the positions of the region to be irradiated with the illumination light on the test specimen 150 and the pixels of the detection system are adjusted such that the center of the beam which has been irradiated to the test specimen 150 in the absence of the AF misalignment is projected onto the middle between the two pixels 104 and 105. When the AF misalignment occurs for the so adjusted detection system and the central position of the beam on the sensor surface is displaced, an output level of a signal 1401 output from the pixel array 104 and a level of a signal 1402 output from the pixel array 105 of the two-stage sensor 103 are changed. This change in signal level corresponds to the AF misalignment amount.

Figure 14B:
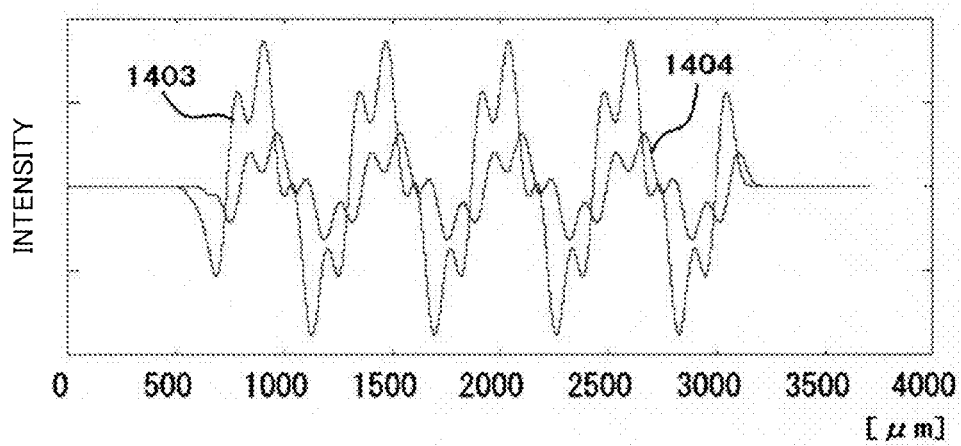
FIG. 14B is a graph showing sensor outputs when reflected/scattered light from a repeated pattern on a test specimen has been detected in the presence of the AF misalignment in the embodiment 1 of the present invention.

FIG. 14B shows an output waveform 1403 from the pixel array 104 and an output waveform 1404 from the pixel array 105 when the reflected/scattered light from the repeated pattern formed on the test specimen 150 is detected by the two-stage sensor 103 when the X-stage 304 moves to scan the beam on the test specimen 150 in a state that the AF misalignment is occurring. Since a constant difference is generated in the signal level between the output waveform 1403 and the output waveform 1404 as shown, it is possible to estimate the AF misalignment amount by adding the output signals from the pixel array 104 and output signals from the pixel array 105 over a certain scan range of the X-stage 304. The addition of the output signals from the pixel array 104 and the output signals from the pixel array 105 over the certain scan range of the X-stage 304 is executed by the height misalignment information calculation unit 112 shown in FIG. 1.

Figure 15:
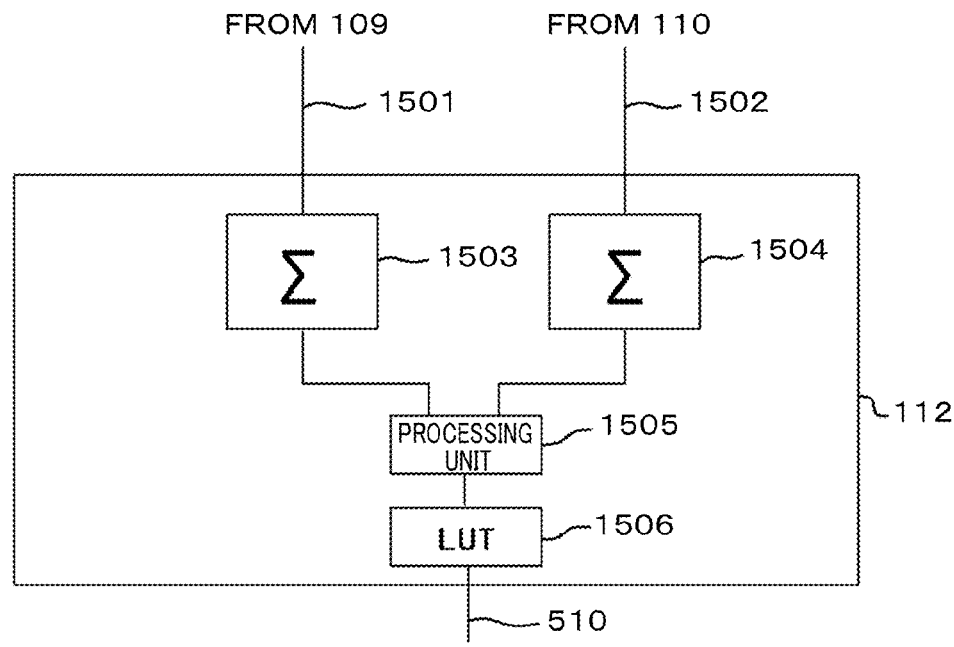
FIG. 15 is a block diagram showing a configuration of a height misalignment information calculation unit in the embodiment 1 of the present invention.

FIG. 15 shows a configuration of the height misalignment information calculation unit 112. 1503 and 1504 are signal adders. A signal 1501 output from the A/D converter 109 is added by the signal adder 1503 and a signal 1502 output from the A/D converter 110 is added by the signal adder 1504 when the X-stage 304 is moving in one direction at a constant speed. Added signals output from the signal adder 1503 and the signal adder 1504 are respectively input into a processing unit 1505 and are normalized by, for example, dividing a signal value output from the signal adder 1503 with a signal value output from the signal adder 1504. A result of normalization is compared with data in a look-up table (LUT) for recording a relationship between an AF misalignment amount which has been set in advance and a normalized value in a comparison unit 1506, and thereby the AF misalignment amount is obtained.

As shown in FIG. 5, information 510A to 510C on the AF misalignment mounts obtained by the height misalignment information calculation unit 112 is sent to the image processing unit 114 and correction of the amount of height misalignment is performed on the difference images 503A to 503C output from the differentiators 502A to 502C using the respective pieces of AF misalignment amount information in the position alignment circuit units 504A to 504C. Incidentally, in a case where 102A and 102C are symmetrically arranged, height misalignments detected with 510A and 510C mutually match in principle. Thus, getting more stable results in the calculation of the AF misalignment amount is possible by calculating an average of the height misalignment amounts detected with 510A and 510C, inputting it into 504A and 504C and using it. In addition, getting further more stable results in the calculation of the AF misalignment amount is possible by performing time-based average processing on the signals of 510A and 510C by taking a feature that the AF misalignment amount is not greatly varied in a short period of time into account. In addition, in a case where 102B is arranged with no inclination, misalignment of images does not occur even when the AF misalignment has occurred. Therefore, 510B and 504B may be eliminated from FIG. 5.

The difference images 505A to 505C subjected to correction of the amount of height misalignment are sent to the integration determining unit 506 and are integrated to generate a three-dimensional vector image. The image generated by the integration and determination unit 506 is sent to the threshold value determination unit 507 in which, then, an image characteristic amount is extracted from each of the defect candidates, an isolated defect candidate is extracted. The isolated defect candidate is separated, by exceeding a previously set threshold value, from a characteristic amount region where the defect candidates are densely present in the characteristic amounts of the defect candidates which are plotted in the three-dimensional space as described in FIG. 7. The extracted defect signal 508 is output to the general control unit 301.

As described above, according to the present embodiment, it becomes possible to perform synthetic processing on the images obtained by imaging from different directions after performing correction of the amount of the AF height alignment, and thereby the defect can be detected with higher sensitivity and the accuracy in classification of the detected defect can be improved.

Embodiment 2

While in the embodiment 1, the example that the two-stage sensor 103 is adopted for the detector 115 is shown, in the present embodiment, an example that a three-stage TDI sensor 1604 is used in place of the two-stage sensor 103 will be described. A configuration of the defect inspection device in the present embodiment is basically the same as that shown in FIGS. 2 and 3, and configurations of the detectors 115A to 115C and configurations or operations of parts of the image processing unit 114 and the general control unit 301 are different from those described in the embodiment 1.

Figure 16:
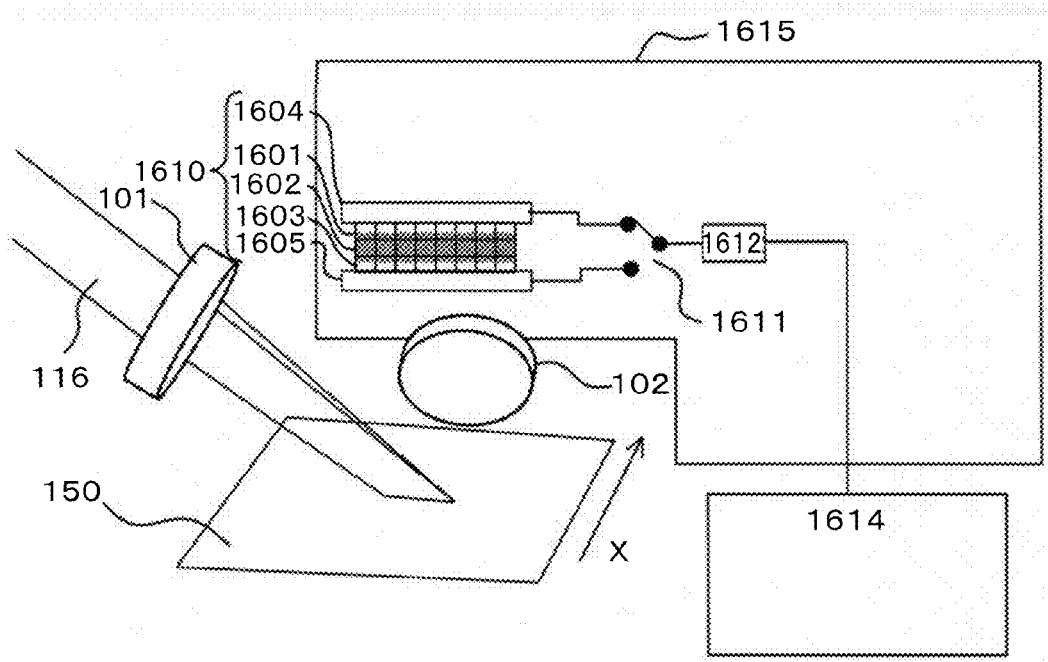
FIG. 16 is a block diagram explaining the principle of an embodiment 2 of the present invention.

FIG. 16 is a diagram explaining the principle of the embodiment 2. The illumination light emitted from a light source (not shown) is squeezed by the lens 101 in one direction (in the X-direction in the case in FIG. 16), is shaped into light which is parallel in a direction perpendicular to it and is obliquely irradiated onto the test specimen 150. At that time, the test specimen 150 is being moved by the X-stage 304 at a constant speed in the X-direction. Light directed toward the detection optical system 102 among the reflected/scattered light from the test specimen 150 which has been irradiated with the illumination light 116 is collected by the detection optical system 102 and is imaged on pixel arrays 1601, 1602, 1603 which are arranged on a light receiving surface of a TDI sensor 1610 of a detector 1615. Signals detected by the pixel arrays 1601, 1602, 1603 are output from a downstream side read out register 1604 or 1605 and are input into an A/D converter 1612 by a change-over switch 1611.

The output signal from the TDI sensor 1610 which has been converted from an analog signal into a digital signal by the A/D converter 1612 is input into and processed by an image processing unit 1614, and thereby a defect on the test specimen 150 is detected.

Since, from the TDI sensor 1610, the signals detected by the respective pixel arrays 1601, 1602, 1603 are sequentially integrated and output from the read out register 1604 or 1605, the output signals are equally affected by the AF misalignment and therefore a circuit corresponding to the height misalignment information calculation unit 112 of the detector 115 in the embodiment 1 is not needed.

Figure 17A:
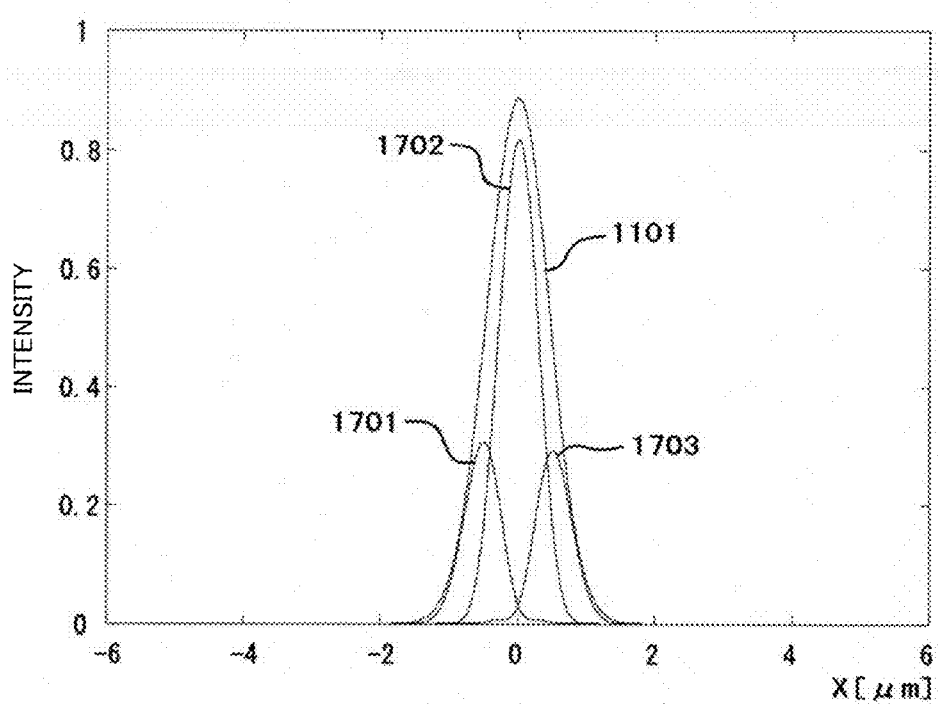
FIG. 17A is a graph showing a beam profile of linear illumination light and pixel-array-based PSFs of a TDI sensor in the embodiment 2 of the present invention.

In FIG. 17A, together with the profile 1101 of the section in the line width direction of the linearly shaped illumination light 116, a result of calculation of the PSF for each of the pixel arrays 1601, 1602, 1603 when the reflected/scattered light from the test specimen 150 irradiated with the illumination light 116 has been detected by the TDI sensor 1610 in the absence of the AF misalignment is plotted as waveforms 1701, 1702, 1703 by superposing with the profile 1101 of the section of the illumination light. Incidentally, calculation was made by setting the pixel size of each of the pixel arrays 1601, 1602, 1603 of the TDI sensor 1610 in the X-stage scanning direction to 0.833 μm.

Outputs from the TDI sensor 1610 can be continuously processed by setting the shift amount of the image detected by the pixel array 1601 and the pixel array 1602 and the shift amount of the image detected by the pixel array 1602 and the pixel array 1603 to the same amount by setting the number of stages of the TDI sensor 1610 to three. In addition, s when using the three-stage TDI sensor, that is, ½ of the moving amount of the stage synchronized with acquisition of the image of one line of the detection system can be calculated by setting α in (Numerical Formula 6) to the pixel size p in the stage moving direction. Also, in this case, s becomes a value smaller than ½ of the pixel size. As in the case in the embodiment 1, if the moving amount of the stage synchronized with acquisition of the image of one line is made equal to the pixel size in the stage moving direction on the test specimen similarly to the case of utilizing the general TDI sensor in this situation, the resolution of the image will be degraded.

In the present embodiment, the case where the number of stages of the pixel arrays of the TDI sensor 1610 is set to three has been described. However, since an image shift amount between adjacent pixel arrays is made different between the central part and the peripheral part with four or more stages of pixel arrays, it becomes impossible to continuously process the outputs from the TDI sensor 1610. Therefore, as for the number of stages of the TDI sensor 1610, two or three stages are suitable.

Figure 17B:
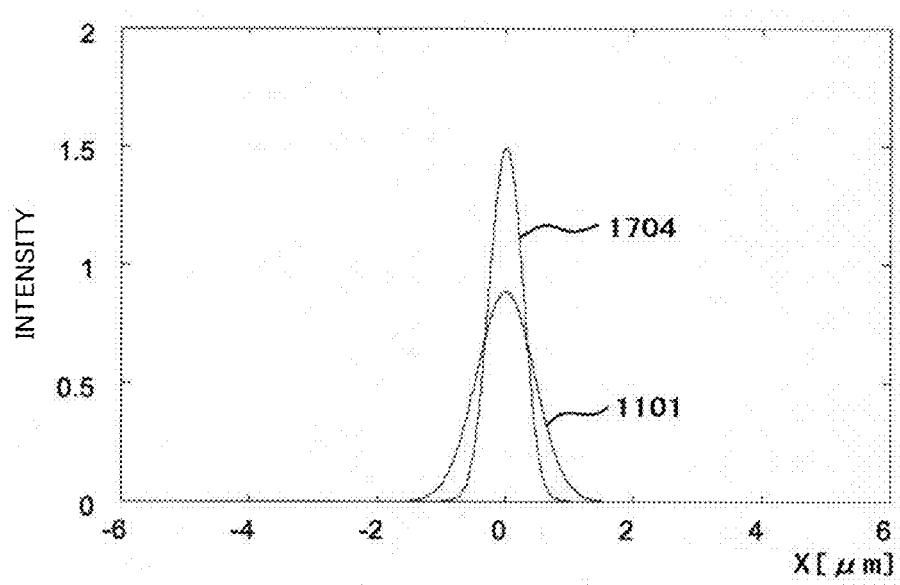
FIG. 17B is a graph showing the beam profile of the linear illumination light and a PSF as a system that outputs from each pixels of the TDI sensor are misaligned by a predetermined amount and are added together in the embodiment 2 of the present invention.

FIG. 17B shows a graph that a PSF 1704 as a system resulting from addition of the PSF waveforms of the respective pixel arrays 1601, 1602, 1603 of the TDI sensor 1610 by shifting them by the shift amount obtained on the basis of (Numerical Formula 5) is plotted by superposing with the beam profile 1101 of the illumination light. From this result, it can be seen that the PSF of the detection system is improved in comparison with the profile of the illumination light.

Figure 18:
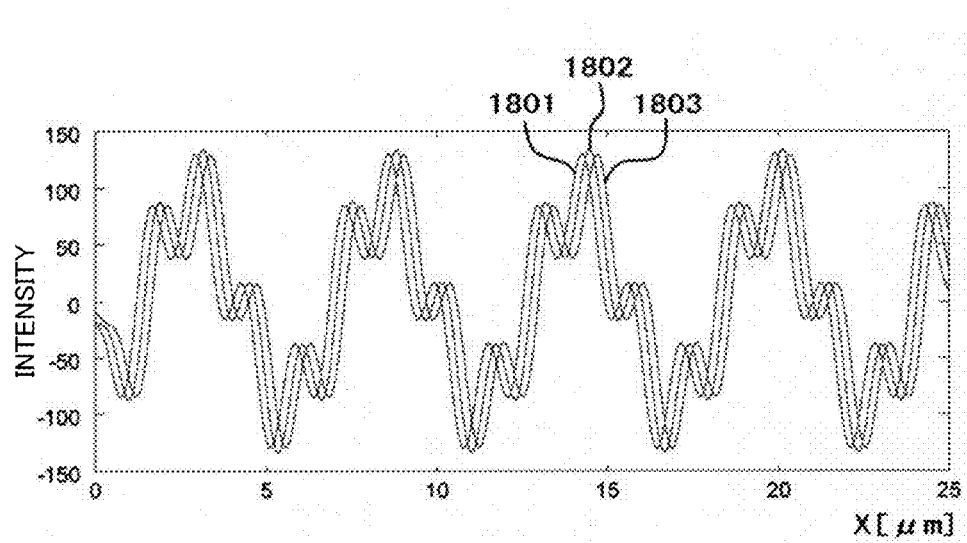
FIG. 18 is a graph showing outputs from the TDI sensor when reflected/scattered light from a repeated pattern on a test specimen has been detected in the presence of the AF misalignment in the embodiment 2 of the present invention.

FIG. 18 shows a result of the simulation of outputs of the TDI sensor 1610 in the case where the AF misalignment is occurring and in the case where the AF misalignment is not occurring when test patterns is illuminated with thinned light by the optical system similar to that shown in FIG. 11A by using the three-stage TDI sensor 1610. It shows the result of the simulation of a sensor output 1802 in the absence of AF misalignment, a sensor output 1801 when the AF misalignment of −0.5 μm is occurring, and a sensor output 1803 when the AF misalignment of +0.5 μm is occurring. It can be seen that the detection signal is greatly varied with occurrence of the AF misalignment. As for the variation range δ of the signal, in a case where the shift amount of the image of the TDI sensor is set to the value calculated by using (Numerical Formula 5) as in the present embodiment (the line width of illumination; 1.5 μm, the pixel size: 1.25 μm), the variation range 6 can be reduced down to ±0.21 μm. Although this is slightly large when compared with the case in the embodiment 1, it is greatly improved when compared with a conventional system that the line width of illumination is wide.

Figure 19:
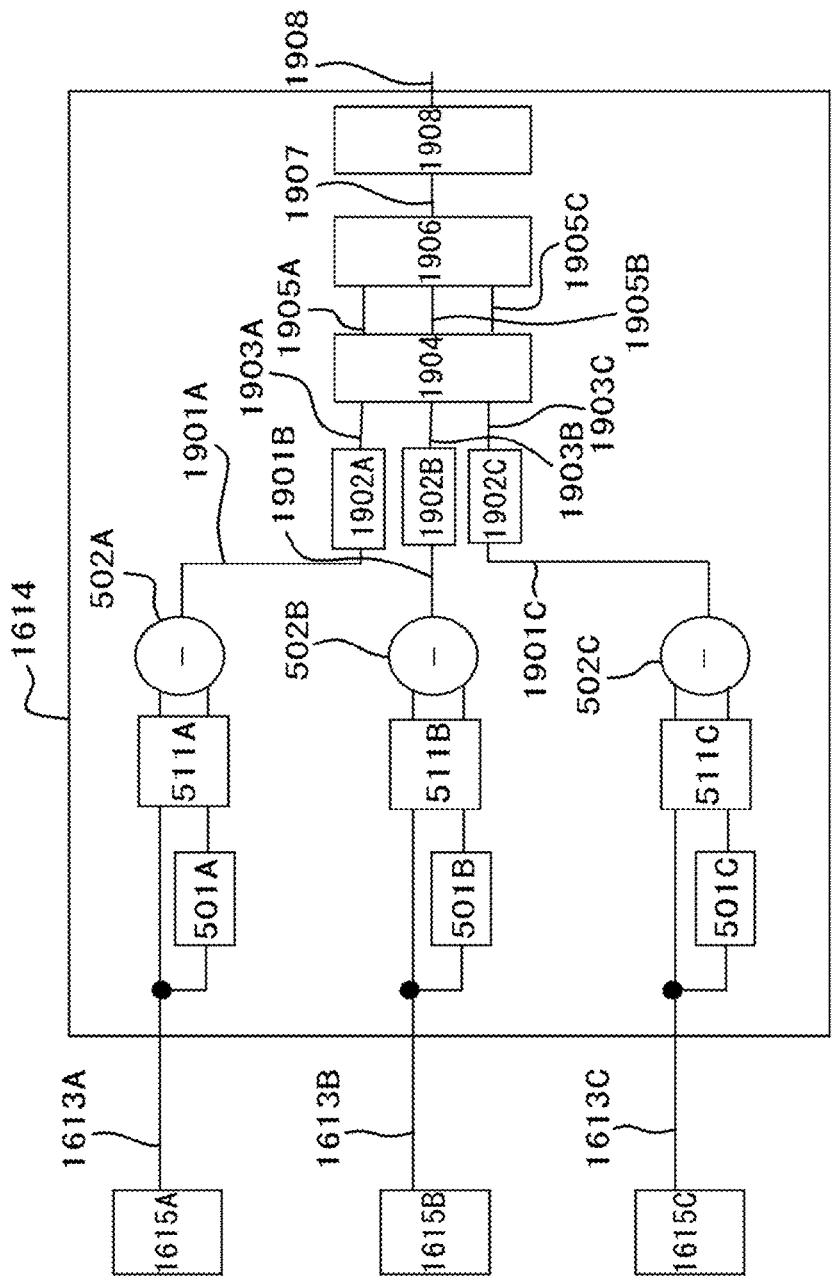
FIG. 19 is a block diagram showing a configuration of an image processing means according to the embodiment 2 of the present invention.

FIG. 19 shows a configuration of the image processing unit 1614 of the defect inspection device in the embodiment 2. Although it is similar to the configuration in the embodiment 1 described in FIG. 5, there is no inputting of signals corresponding to the output signals 510A-510C from the height misalignment information calculation unit 112 described in FIG. 5.

In the configuration shown in FIG. 19, one of the signals branched from an output 1613A from a first detector 1615A is input into the buffer memory 501A, and position alignment is performed by the first position alignment processing unit 511A as described in FIG. 5. The other branched signal is input into the differentiator 502A. A signal input in the buffer memory 501A in advance which is a signal that is obtained by detecting patterns of the same shape on the test specimen 150 or a signal that is obtained by detecting patterns in the same regions of the adjacent dies on the test specimen 150 is set as a reference signal. Then a difference between the other branched signal and the reference signal is calculated (cell comparison or die comparison). A calculated difference image 1901A is compared with a first threshold value signal level which has been set in advance in a temporary defect determination unit 1902A, and a pseudo defect is removed from the difference image 1901A. A signal 1903A from which the pseudo defect signal has been removed is input into an AF misalignment calculation unit 1904.

An output 1613B from a second detector 1615B and an output 1613C from a third detector 1615C are similarly processed, are compared with the first threshold value signal level which has been set in advance in a temporary defect determination units 1902B and 1902C, and signals 1903B and 1903C from which the pseudo defect signal has been removed are input into the AF misalignment calculation unit 1904.

Figure 20:
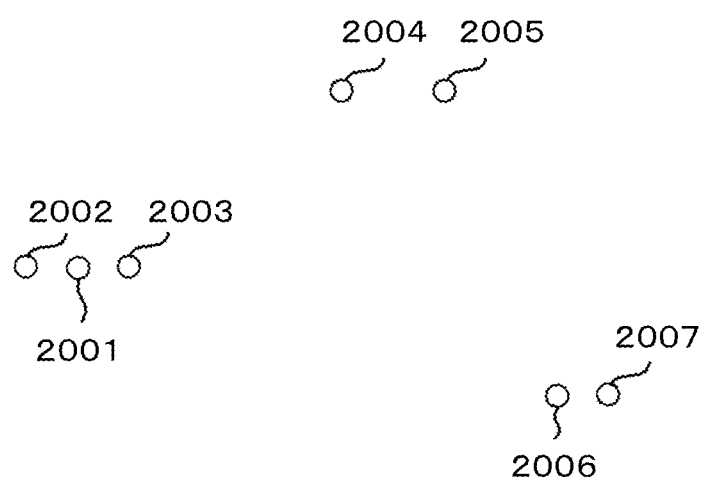
FIG. 20 is a diagram plotting arrangement of defect candidates from outputs of the TDI sensor, explaining a method of correcting an AF misalignment amount of outputs of the TDI sensor in the image processing means according to the embodiment 2 of the present invention.

A method of obtaining the AF misalignment amount in the AF misalignment calculation unit 1904 will be described using FIG. 20. In FIGS. 20, 2001 and 2006 designate positions of defect candidates detected by the first detector 1615A, 2002 and 2004 designate positions of defect candidates detected by the second detector 1615B, and 2003 and 2007 designate positions of defect candidates detected by the third detector 1615C. Assuming that the defect candidates which are present in a comparatively short range have the same AF misalignment amount, the AF misalignment amount is estimated from coordinate information of the defect candidates among which a corresponding relationship is best (in the case in FIGS. 20, 2001, 2002 and 2003). Then, height misalignment among the signals 1903A to 1903C from which the pseudo defect signal has been removed is corrected using information on the estimated AF misalignment amount. The signals 1905A to 1905C corrected in height misalignment by the AF misalignment calculation unit 1904 are input into a integration determining unit 1906, are combined into a three-dimensional vector differential image which is, then, compared with a threshold value which has been set in advance by a threshold value determination unit 1908 to extract a defect therefrom. Information 1909 on the extracted defect is output to the general control unit 301.

According to the present embodiment, it becomes possible to perform synthetic processing after performing correction of the amount of the AF height misalignment on the images obtained by imaging from different directions, and therefore the defect can be detected with higher sensitivity and the accuracy in classification of the detected defect can be improved.

Embodiment 3

Figure 21:
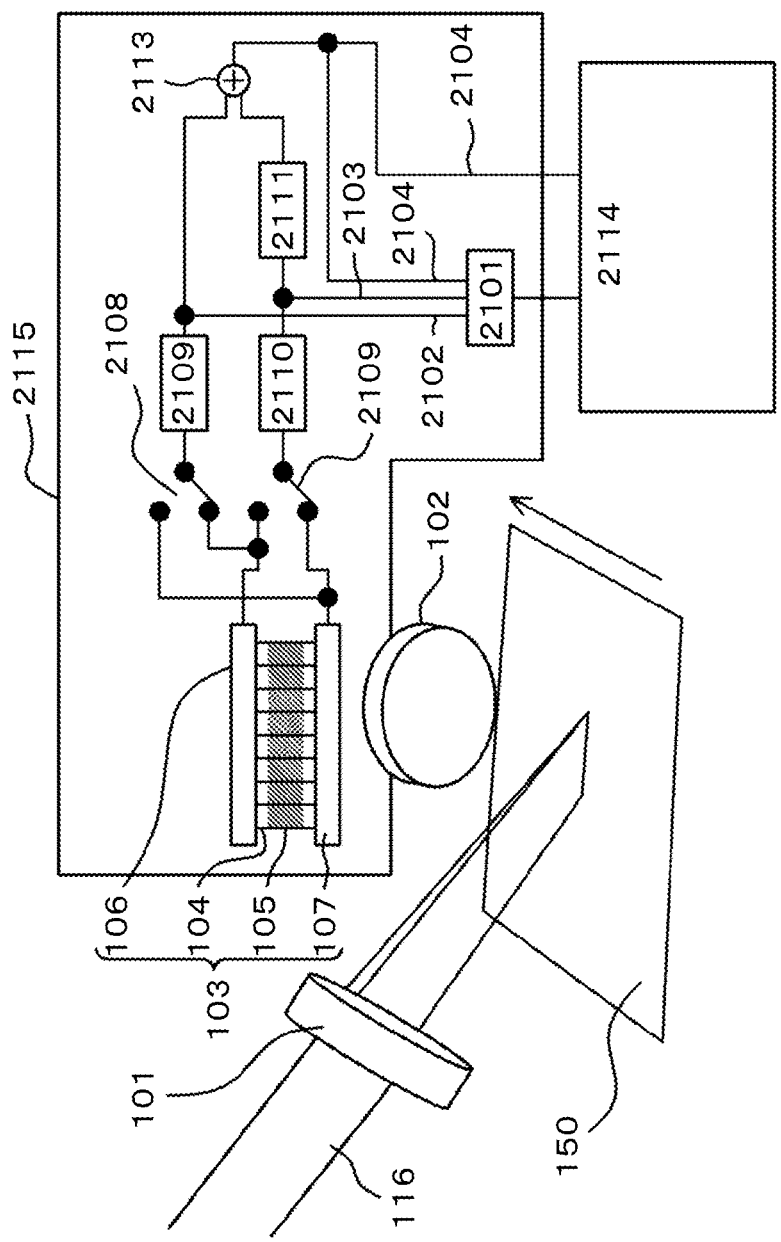
FIG. 21 is a block diagram explaining the principle of an embodiment 3 of the present invention.

In the present embodiment, a system for determining the AF misalignment on the basis of a pattern to be detected is shown FIG. 21. The configuration of the defect inspection device according to the present embodiment is basically the same as the configuration shown in FIGS. 2 and 3 in the embodiment 1, and only parts of the configurations of the detectors 115A to 115C are different from the configurations and operations described in the embodiment 1. In the embodiment 1, the two-stage sensor 103 is adopted in the detector 115 and the misalignment between detection positions caused by the AF misalignment has been calculated by the height misalignment information calculation unit 112. The height misalignment information calculation unit 112 has calculated the height by evaluating the contrast ratio calculated from the signal output from the A/D converter 109 and the signal output from the A/D converter 110 as shown in FIG. 15.

On the other hand, in the present embodiment, as shown in FIG. 21, the AF misalignment is calculated by using a height misalignment information calculation unit 2101 in place of the height misalignment information calculation unit 112. In the configuration shown in FIG. 21, the two-stage sensor 103 is the same as that described in the embodiment 1 using FIG. 1. In addition, switches 2108 and 2109 switch the outputs from the read out registers 106 and 107 of the two-stage sensor 103 in accordance with the moving direction of the test specimen 150. A signal 2102 output from an A/D converter 2109, a signal 2103 output from an A/D converter 2110 and a signal 2104 added and synthesized by an adder 2113 are input into the height misalignment information calculation unit 2101.

Figure 22:
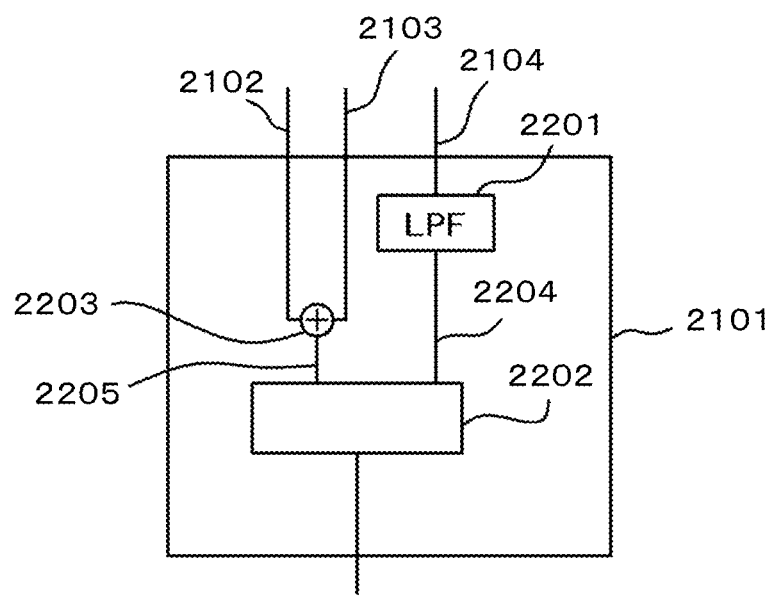
FIG. 22 is a block diagram showing a configuration of a height misalignment information calculation unit in the embodiment 3 of the present invention.

Processing of the height misalignment information calculation unit 2101 will be described using FIG. 22. 2201 is a low pass filter for restricting a high spatial frequency in the stage scanning direction shown by an arrow in FIG. 21 relative to the signal of the signal 2104 added and synthesized by the adder 2113 to output a signal 2204. 2203 is an adder for adding together the signal 2102 output from the A/D converter 2109 and the signal 2103 output from the A/D converter 2110 to output a signal 2205. Since this signal 2205 is an image, the resolution of which is degraded in the stage scanning direction relative to the signal 2104 added and synthesized by the adder 2113, the signal 2204 and the signal 2205 are extremely similar images. Therefore, the misalignment amount is calculated by pattern-matching the signal 2204 and the signal 2205 by a pattern matching unit 2202. As for the signal 2205, the position of the pattern is hardly changed with the AF misalignment. On the other hand, as for the signal 2204, the position of the pattern is changed with the AF misalignment. Thus, it becomes possible to calculate the AF misalignment by obtaining the misalignment amount of the signal 2204 using the signal 2205 as a reference.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

DESCRIPTION OF REFERENCE NUMERALS

100 . . . inspection optical system, 101 . . . lens, 102, 102A, 102B, 102C . . . detection optical system, 103 . . . two-stage sensor, 112 . . . height misalignment information calculation unit, 113 . . . adder, 114 . . . image processing unit, 115, 115A, 115B, 115C . . . detector, 201 . . . light source unit, 202 . . . collecting lens, 203 . . . collecting lens, 204 . . . photo-detector, 205 . . . height detection unit, 301 . . . general control unit, 302 . . . stage control means, 303 . . . Z-stage, 304 . . . X-stage, 305 . . . Y-stage, 501A, 501B, 501C . . . buffer memory, 502A, 502B, 502C . . . differentiator, 504A, 504B, 504C . . . position alignment circuit unit, 506 . . . integration determining unit, 507 . . . threshold value determination unit, 1610 . . . TDI sensor, 1614 . . . image processing unit, 1615 . . . detector, 1902A, 1902B, 1902C . . . temporary defect determination unit, 1904 . . . AF misalignment calculation unit, 1906 . . . integration determining unit, 1908 . . . threshold value determination unit.

The invention claimed is:

1. A defect inspection device, comprising:
a stage unit which is movable at least in one direction with a test specimen placed thereon; a light irradiation unit which irradiates the test specimen placed on the stage unit with linearly shaped light from a direction inclined relative to a normal direction of a surface of the stage on which the test specimen is placed;
a first light collecting/detecting unit which collects and detects light reflected/scattered in a first direction from the test specimen irradiated with the linearly shaped light by the light irradiation unit;
a second light collecting/detecting unit which collects and detects light reflected/scattered in a second direction from the test specimen irradiated with the linearly shaped light by the light irradiation unit;
a processing unit which processes a detection signal output from the first light collecting/detecting unit and a detection signal output from the second light collecting/detecting unit to detect a defect on the test specimen; and
a control unit which controls the stage unit, the light irradiation unit, the first light collecting/detecting unit, the second light collecting/detecting unit and the processing unit,
wherein each of the first light collecting/detecting unit and the second light collecting/detecting unit has a photoelectric converter provided with a plurality of optical sensor arrays, and
the processing unit obtains misalignment of a focal position of the first light collecting/detecting unit relative to a surface of the test specimen by using detection signals from the plurality of optical sensor arrays of the first light collecting/detecting unit, obtains misalignment of a focal position of the second light collecting/detecting unit relative to the surface of the test specimen by using detection signals from the plurality of optical sensor arrays of the second light collecting/detecting unit, corrects the detection signal output from the first light collecting/detecting unit and the detection signal output from the second light collecting/detecting unit in accordance with the obtained misalignment of the focal position of the first light collecting/detecting unit and the obtained misalignment of the focal position of the second light collecting/detecting unit, combines together the detection signal output from the first light collecting/detecting unit and the detection signal output from the second light collecting/detecting unit which have been corrected to detect the defect on the test specimen.

2. The defect inspection device according to claim 1, further comprising: a third light collecting/detecting unit which collects and detects light reflected and scattered in a third direction from the test specimen irradiated with the linearly shaped light by the light collection and irradiation unit and having a photoelectric converter provided with a plurality of optical sensor arrays.

3. The defect inspection device according to claim 1, wherein each of the first light collecting/detecting unit and the second light collecting/detecting unit is provided with a dual line sensor having two optical sensor arrays as a photo-detector.

4. The defect inspection device according to claim 1, wherein each of the first light collecting/detecting unit and the second light collecting/detecting unit is provided with a spatial filter for light-shielding a diffracted light pattern which is generated from a repeated pattern formed on the test specimen and detects light transmitted through the spatial filter.

5. The defect inspection device according to claim 1, further comprising: a height detection unit which optically detects a height of the test specimen surface.

6. A defect inspection device, comprising:
a stage unit which is movable at least in one direction with a test specimen placed thereon;
a light irradiation unit which irradiates the test specimen placed on the stage unit with linearly shaped light from a direction inclined relative to a normal direction of a surface of the stage on which the test specimen is placed;
a first light collecting/detecting unit which collects and detects light reflected/scattered in a first direction from the test specimen irradiated with the linearly shaped light by the light irradiation unit;
a second light collecting/detecting unit which collects and detects light reflected/scattered in a second direction from the test specimen irradiated with the linearly shaped light by the light irradiation unit;
a processing unit which processes a detection signal output from the first light collecting/detecting unit and a detection signal output from the second light collecting/detecting unit to detect a defect on the test specimen; and
a control unit which controls the stage unit, the light irradiation unit, the first light collecting/detecting unit, the second light collecting/detecting unit and the processing unit, wherein
each of the first light collecting/detecting unit and the second light collecting/detecting unit has a photoelectric converter provided with a plurality of optical sensor arrays,
the control unit controls the stage unit to continuously move the stage unit in the first direction and controls the photoelectric converter of the first light collecting/detecting unit and the photoelectric converter of the second light collecting/detecting unit to detect reflected and scattered light from the test specimen irradiated with the linearly shaped light by the light irradiation unit in synchronization with movement of the stage unit, and
the control unit further controls the processing unit to process detection signals output from the photoelectric converter of the first light collecting/detecting unit and the photoelectric converter of the second light collecting/detecting unit based on height misalignment at a timing different from the motive with movement of the stage unit, corrects the detection signal output from the first light collecting/detecting unit and the detection signal output from the second light collecting/detecting unit in accordance with the obtained misalignment of the focal position of the first light collecting/detecting unit and to combine together the detection signals which have been output from the photoelectric converter of the first light collecting/detecting unit and the photoelectric converter of the second light collecting/detecting unit and have been processed at the timing different from the synchronization, thereby detecting a defect on the test specimen.

7. The defect inspection device according to claim 6, further comprising:
a third light collecting/detecting unit which collects and detects light reflected and scattered in a third direction from the test specimen irradiated with the linearly shaped light by the light collection and irradiation unit and having a photoelectric converter provided with a plurality of optical sensor arrays.

8. The defect inspection device according to claim 6, wherein each of the first light collecting/detecting unit and the second light collecting/detecting unit is provided with a dual line sensor having two optical sensor arrays as a photo-detector.

9. The defect inspection device according to claim 6, wherein each of the first light collecting/detecting unit and the second light collecting/detecting unit is provided with a spatial filter for light-shielding a diffracted light pattern which is generated from a repeated pattern formed on the test specimen and detects light transmitted through the spatial filter.

10. The defect inspection device according to claim 6, further comprising:
a height detection unit which optically detects a height of the test specimen surface.

11. A defect inspection method, comprising:
while moving a stage with a test specimen placed thereon in one direction, irradiating a surface of the test specimen with linearly shaped light which is long in a direction rectangular to the one direction that the stage moves from a direction inclined relative to a normal direction of the surface of the test specimen;
collecting and detecting light reflected/scattered in a first direction from the surface of the test specimen irradiated with the linearly shaped light by a first light collecting/detecting unit provided with a plurality of optical sensor arrays;
collecting and detecting light reflected/scattered in a second direction from the surface of the test specimen irradiated with the linearly shaped light by a second light collecting/detecting unit provided with a plurality of optical sensor arrays;
obtaining misalignment of a focal position of the first light collecting/detecting unit relative to the surface of the test specimen by using detection signals from the plurality of optical sensor arrays and output from the first light collecting/detecting unit and obtaining misalignment of a focal position of the second light collecting/detecting unit relative to the surface of the test specimen by using detection signals from the plurality of optical sensor arrays and output from the second light collecting/detecting unit;
correcting the detection signal output from the first light collecting/detecting unit and the detection signal output from the second light collecting/detecting unit in accordance with the misalignment of the focal position of the first light collecting/detecting unit and the misalignment of the focal position of the second light collecting/detecting unit which have been so obtained; and
combining together the detection signal output from the first light collecting/detecting unit and the detection signal output from the second light collecting/detecting unit which have been so corrected to detect a defect on the test specimen.

12. The defect inspection method according to claim 11, further comprising:
collecting and detecting light reflected/scattered in a third direction from the surface of the test specimen irradiated with the linearly shaped light by a third light collecting/detecting unit provided with a plurality of optical sensor arrays; and
obtaining misalignment of a focal position of the third light collecting/detecting unit relative to the surface of the test specimen by using detection signals from the plurality of optical sensor arrays and output from the third light collecting/detecting unit, correcting the detection signal output from the third light collecting/detecting unit in accordance with the obtained misalignment of the focal position of the third light collecting/detecting unit, and combining together the corrected detection signal output from the third light collecting/detecting unit, and the detection signal output from the first light collecting/detecting unit and the detection signal output from the second light collecting/detecting unit which have been corrected to detect the defect on the test specimen.

13. The defect inspection method according to claim 11, further comprising:
detecting the light collected by the first light collecting/detecting unit and reflected/scattered in the first direction from the surface of the test specimen by two optical sensor arrays of the first light collecting/detecting unit to obtain the misalignment of the focal position of the first light collecting/detecting unit relative to the surface of the test specimen by using a detection signal from each of the two optical sensor arrays, and detecting the light collected by the second light collecting/detecting unit and reflected/scattered in the second direction from the surface of the test specimen by two optical sensor arrays of the second light collecting/detecting unit to obtain the misalignment of the focal position of the second light collecting/detecting unit relative to the surface of the test specimen by using a detection signal from each of the two optical sensor arrays.

14. The defect inspection method according to claim 11, wherein each of the first light collecting/detecting unit and the second light collecting/detecting unit detects light from which a diffracted light pattern generated from a repeated pattern formed on the test specimen has been shielded.

15. The defect inspection method according to claim 11, further comprising: when the surface of the test specimen is being irradiated with the linearly shaped light while moving the stage with the test specimen placed thereon in one direction, optically detecting a height of the test specimen surface to control the height of the test specimen surface by moving the stage up and down on the basis of information on the detected height.

* * * * *